United States Patent
Sabourian-Tarwe

(10) Patent No.: US 9,728,098 B2
(45) Date of Patent: Aug. 8, 2017

(54) INTERACTIVE CULINARY GAME APPLICATIONS

(71) Applicant: Chef Koochooloo, Inc., Mountain View, CA (US)

(72) Inventor: Layla Sabourian-Tarwe, Mountain View, CA (US)

(73) Assignee: Chef Koochooloo, Inc., Mountain View, CA (US)

( * ) Notice: Subject to any disclaimer, the term of this patent is extended or adjusted under 35 U.S.C. 154(b) by 238 days.

(21) Appl. No.: 14/690,137

(22) Filed: Apr. 17, 2015

(65) Prior Publication Data

US 2015/0302762 A1    Oct. 22, 2015

Related U.S. Application Data

(60) Provisional application No. 61/981,540, filed on Apr. 18, 2014.

(51) Int. Cl.
| | | |
|---|---|---|
| G09B 5/00 | (2006.01) | |
| G09B 5/02 | (2006.01) | |
| G09B 7/00 | (2006.01) | |
| G09B 19/00 | (2006.01) | |
| G06Q 50/12 | (2012.01) | |
| G06F 19/00 | (2011.01) | |

(52) U.S. Cl.
CPC .......... *G09B 7/00* (2013.01); *G06F 19/3475* (2013.01); *G06Q 50/12* (2013.01); *G09B 5/00* (2013.01); *G09B 5/02* (2013.01); *G09B 19/0092* (2013.01)

(58) Field of Classification Search
CPC ... G09B 5/00; G09B 5/02; G09B 7/00; G09B 19/0092; G06F 19/3475; G06Q 50/12
USPC ......................................................... 434/127
See application file for complete search history.

(56) References Cited

U.S. PATENT DOCUMENTS 2,768,452 A * 10/1956 Littlejohn ............. A63F 3/0478
                                                           273/157 R
5,832,446 A * 11/1998 Neuhaus ................. G06Q 50/12
                                                              434/127

(Continued)

OTHER PUBLICATIONS

Playful chef Deluxe Cooking Kit with Blue Apron (Ages 6 and up). Author Unknown, Retrieved on Jun. 11, 2017 [Retrieved online from Mindware Inc.] <http://www.mindware.orientaltrading.com/playful-chef-deluxe-cooking-kit-with-blue-apron-ages-6-and-up-a2-66004.fltr>.*

(Continued)

*Primary Examiner* — Nikolai A Gishnock
(74) *Attorney, Agent, or Firm* — Perkins Coie LLP

(57) ABSTRACT

A culinary application enables consumers, such as a parent and a child, to engage in discovering cooking recipes in a fun interactive way while also learning about various topics, including math, science, geography and social responsibility. The culinary application can be focused towards children of various age groups. Consumers engage with the culinary game application in an interactive way to search for recipes based on various user preferences such as a favorite ingredient, a diet, a cooking duration, an ethnic group, a particular country, etc. The culinary application can also present trivia related to a recipe, such as benefits of a particular ingredient in the recipe, information about a country where a dish is popular, math involved in measurements of ingredients, etc. The culinary application can generate separate sets of instructions for a parent and child.

29 Claims, 21 Drawing Sheets

(56) References Cited

U.S. PATENT DOCUMENTS

| | | | | |
|---|---|---|---|---|
| 6,370,513 | B1* | 4/2002 | Kolawa | G06Q 30/02 705/15 |
| 6,646,659 | B1* | 11/2003 | Brown | G06Q 30/02 705/15 |
| 6,975,910 | B1* | 12/2005 | Brown | G06F 19/3475 700/90 |
| 8,152,528 | B2* | 4/2012 | Alm | G09B 19/00 273/236 |
| 8,657,604 | B2* | 2/2014 | Gilchrist | G09B 19/00 434/127 |
| 9,011,153 | B2* | 4/2015 | Bennett | G09B 5/00 434/127 |
| 2007/0141539 | A1* | 6/2007 | Lemieux | G09B 19/0092 434/107 |
| 2009/0047638 | A1* | 2/2009 | Jansen | G09B 19/0092 434/127 |
| 2009/0077007 | A1* | 3/2009 | Schwarzberg | G06F 19/3475 707/999.001 |
| 2011/0300519 | A1* | 12/2011 | Lemieux | G09B 19/0092 434/127 |
| 2012/0094258 | A1* | 4/2012 | Langheier | G06F 19/3406 434/127 |
| 2013/0149678 | A1* | 6/2013 | Tokuda | G09B 19/0092 434/127 |
| 2013/0222406 | A1* | 8/2013 | Wolfe | G06T 11/206 345/582 |
| 2013/0224694 | A1* | 8/2013 | Moore | G09B 19/0092 434/127 |
| 2013/0260346 | A1* | 10/2013 | Wood | G09B 5/00 434/156 |
| 2013/0325640 | A1* | 12/2013 | Morgan | G06Q 50/12 705/15 |
| 2014/0011165 | A1* | 1/2014 | Childress | G09B 19/0092 434/127 |
| 2014/0143020 | A1* | 5/2014 | Wolfe | G06T 11/206 705/7.33 |
| 2014/0272817 | A1* | 9/2014 | Park | G09B 5/02 434/127 |
| 2014/0322678 | A1* | 10/2014 | Briancon | G09B 19/0092 434/127 |
| 2015/0132725 | A1* | 5/2015 | Okubo | G09B 19/0092 434/127 |
| 2016/0379507 | A1* | 12/2016 | Reale | G09B 5/125 434/238 |

OTHER PUBLICATIONS

"Big Fork, Little Fork," by Kraft New Services, Inc., iTunes Apps Store, Apple, Inc. Software Application [online]. 2 pages, Jun. 8, 2012 [retrieved on May 26, 2015]. Retrieved from the internet: <https://itunes.apple.com/us/app/big-fork-little-fork/id379783460?mt=8>.

"Cooking Fun for Kids: Healthy Playful Recipes, Food Games, and Videos for Kids in the Kitchen by Bean Sprouts," by Playrific, Inc., iTunes Apps Store, Apple, Inc. Software Application [online]. 2 pages, Oct. 14, 2014 [retrieved on May 26, 2015]. Retrieved from the internet: <https://itunes.apple.com/us/app/cooking-fun-for-kids-healthy/id799530322?mt=8>.

"Explore, Play and Learn Safely!" Playrific, Inc., iOS & Android Software Applications [online]. 2 pages, 2015 [retrieved on May 26, 2015]. Retrieved from the internet: <http://playrific.com/apps>.

"Great British Chefs Kids," by Great British Chefs, Ltd., iTunes Apps Store, Apple, Inc. Software Application [online]. 2 pages, Nov. 21, 2013 [retrieved on May 26, 2015]. Retrieved from the internet: <https://itunes.apple.com/us/app/great-british-chefs-kids/id639551924?mt=8>.

"Nicolas' Garden," by AppMatrix, Inc., iTunes Apps Store, Apple, Inc. Software Application [online]. 2 pages, May 6, 2014 [retrieved on May 26, 2015]. Retrieved from the internet: <https://itunes.apple.com/us/app/nicolas-garden/id645700494?mt=8>.

"WeCookit Recipes Cooking Tips," by Mango Tree Ltd., iTunes Apps Store, Apple, Inc. Software Application [online]. 2 pages, Mar. 18, 2014 [retrieved on May 26, 2015]. Retrieved from the internet: <https://itunes.apple.com/us/app/wecookit-recipes-cooking-tips/id731343271?mt=8>.

"WeCookit Recipes Cooking Tips," Mango Tree Ltd. Software Application [online]. 2 pages, 2013 [retrieved on May 26, 2015]. Retrieved from the internet: <http://www.we-cookit.com/>.

* cited by examiner

200

Argentina

Country we are exploring: Argentina
Continent: South America
Capital: Buenos Aires
Population: 41.5 million

Official language(s): Spanish

Suggestion for Fun Image: Little Chefs dancing to Tango

Fun Fact:
Argentina's national sport is pato, a game played on horseback. It is similar to both polo and basketball. The word *pato* means "duck" in Spanish, as early versions of the sport used a live duck inside a basket, instead of a ball.

English Recipe Name: Quince Paste Tart( vegetarian)

Name of dish in native country: Pasta Frola de Dulce de Membrillo

Prep & Cook time: 1 hour and 45 minutes

Type of dish: Dessert

Recommended season or holiday: Thanksgiving, Christmas, Easter

Serving size: 6-10

Ingredient spotlight:
Dulce de Membrillo
Dulce de Membrillo, or quince paste is made from quince, a low calorie fruit that contains several vital antioxidants that keep the body young and healthy. The fruit is also full of minerals.
Like vitamins, minerals help your body grow, develop, and stay healthy. The body uses minerals to perform many different functions — from building strong bones to transmitting nerve impulses. Some minerals are even used to make hormones or maintain a normal heartbeat.
...
...

*FIG. 2A*

Tools:
Tart pan
Rolling pin

Ingredients:
- 4 cups flour
- 2 tbsp baking powder
- 1 tsp salt
- 1 cup sugar
- 2 sticks butter
- 2 tsp vanilla extract
- 2 eggs
- 2 egg yolks
- 4 tbsp milk
- 2 cups quince paste (dulce de membrillo)
- ½ cup pineapple preserves (optional)
- ½ cup raspberry jam (optional)

205

Big Chef Duties:
1. Add dulce de membrillo (quince paste), pineapple and raspberry jam to a small pot with 1 or 2 tablespoons of water, and cook at low heat, stirring frequently.
2. Remove pot from heat and let it cool.
3. Wrap dough in plastic and chill for about 30 minutes.
4. Preheat oven to 350 degrees.
5. Help the Little Chefs add the filling into the pie dish before continuing.
6. Roll the remaining dough into a circle and cut thin strips of dough.
7. Along with the Little Chef, make a lattice pattern over the top of the tart
8. Cook in the oven until golden brown (about 30 minutes).

Little Chef Duties:
1. Mix the dry ingredients (flour, salt, baking powder and sugar) in a bowl using a whisk.

210

2. Cut the butter into small pieces and mix into ingredients until well blended.
3. Add milk, egg and egg yolk to the dry mix. Make sure mix is not too wet or too crumbly; you can add an extra tablespoon of flour or milk to adjust.
4. Butter a 9 inch pie dish.
5. Roll about ¾ of the dough on a floured surface and make it a circle big enough to cover all of the pie dish, place in buttered dish.
6. Spread the filling prepared by Big Chef into the dish.

*FIG. 2B*

Learn while you wait:
Math: Have the students count the ingredients, divide and multiply based on doubling the recipe, etc
Science:
When a pie or cake bakes, the whole protein network in the mix hardens due to the heat in the oven. The color of the dough changes as the protein hardens and that is what gives pie dough or cake dough a darker color.

Presentation:
Sprinkle with powdered sugar and serve warm!

**Teach the kids how to say *Bon Appetit* in the language of this recipe:**
Buen Provecho!

Did you know?
In Argentina, about 30% of people don't have enough money to live. This means 3 out of 10 people. This is especially a problem in rural areas that are far from large cities. Children may not go to the doctor as often as they should. They also may not be able to go to school because they need to work to make money for their family to eat.

Conversation Igniters:
If someone that you knew didn't have enough money to eat, what would you do? Do you think that it's okay that children have to work instead of go to school? How would you feel if you couldn't go to school?

Take Action:

http://www.humanium.org/en/argentina/

*FIG. 2C*

INTERACTIVE CULINARY GAME APPLICATIONS

CROSS-REFERENCE TO RELATED APPLICATION(S)

This application claims the benefit of U.S. Provisional Application Ser. No. 61/981,540 titled "INTERACTIVE CULINARY GAME APPLICATIONS" filed Apr. 18, 2014, which is incorporated herein by reference for all purposes in its entirety.

BACKGROUND

While innovations arise in many areas of everyday life, little has changed with regards to recipes and culinary instructions. Current tools for recipe delivery are typically naïve; they present recipes generally in a flat approach that provides bare-bone publications of information (e.g., printed materials, instructional videos, static webpages, or semantic searches), lacking in experience to properly meet the realities of day-to-day cooking faced by the ordinary consumer. Further, delivery of the recipes through these publications provide no insights to the cooking experience, such as food knowledge, nutrition, wellness education, meal planning, a better execution of cooking at home, or how to save money on meals. Some online cooking applications present recipes to the users based on various user preferences. However, these cooking applications are generally targeted to users of adult age range. These cooking applications are typically not child-friendly. The cooking applications offer minimum to none insight to children who are interested in cooking, or to parents who want to engage their children in cooking. Some of the cooking applications have user interfaces that are less-intuitive, complex and not user friendly, which can typically discourage a user from using the cooking application. Further, some of these cooking applications also lack educational features, that is, they fail to provide any educational information to the children.

BRIEF DESCRIPTION OF THE DRAWINGS

FIGS. 2A, 2B and 2C, collectively referred to as FIG. 2, is an example template of a recipe and trivia that can be generated using the culinary application of FIG. 1, consistent with various embodiments.

DETAILED DESCRIPTION

Figure 1:
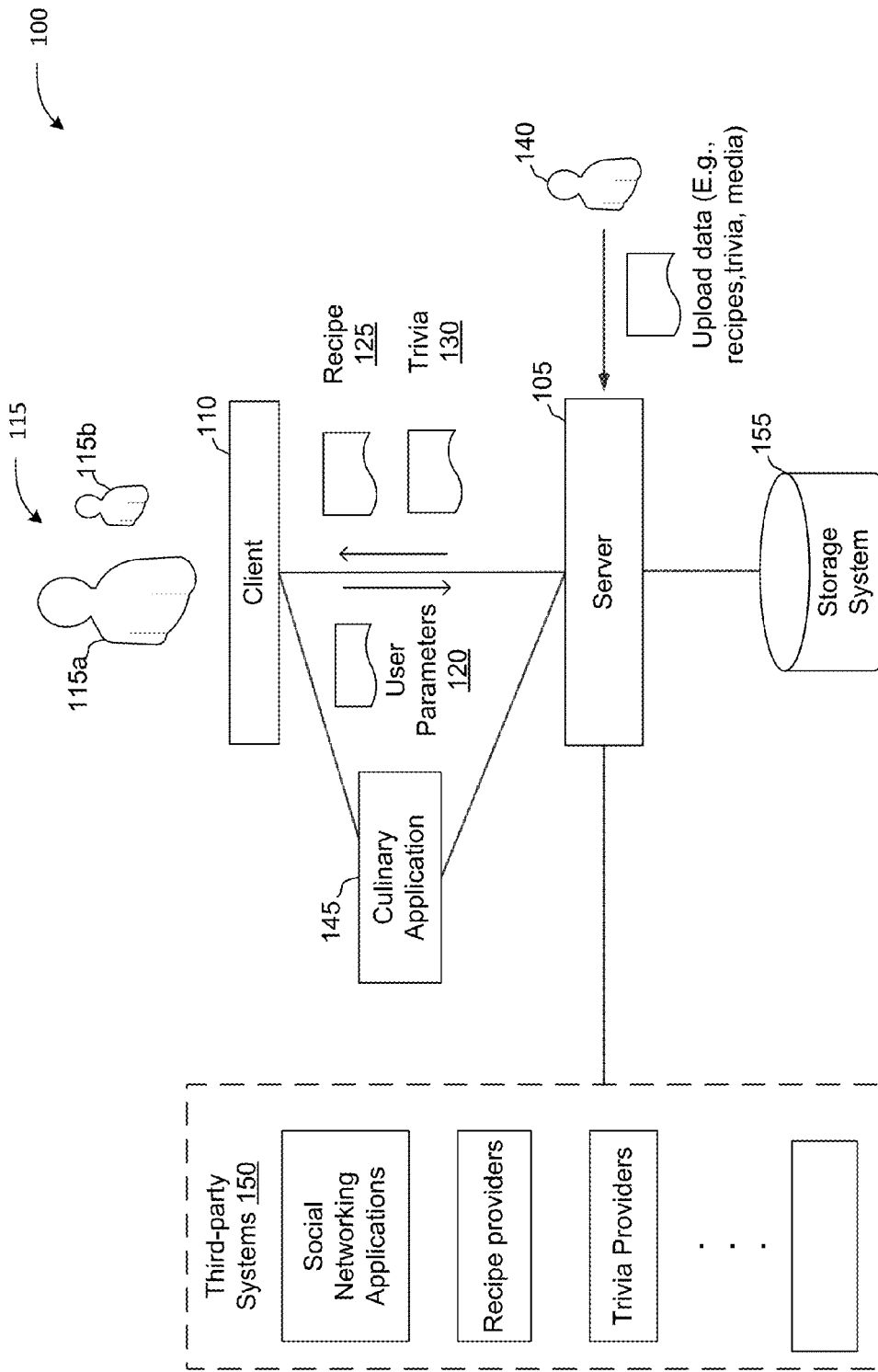
FIG. 1 is a block diagram illustrating an environment in which a culinary application can be implemented.

Introduced here is a technology for providing an interactive culinary experience ("the technology"). The technology includes a culinary game application ("culinary application") that enables consumers, such as a parent and a child, to engage in discovering cooking recipes in an interactive way and that is interesting to the child while also learning about various topics, including math, science, geography and social responsibility. The culinary application can be configured for children of various age groups. For example, the recipes, the look and feel of a graphical user interface (GUI) of the culinary application, e.g., images, videos, icons, can be configured in a way that is appropriate or attractive to a specified age group. The users engage with the culinary application in an interactive way to search for recipes based on various user preferences such as a favorite ingredient, vegetable, fruit of the consumer, a type of occasion, a cooking duration, a type of ingredient, a type of diet, equipment that may be required, an ethnic group, a particular culture, a particular country, etc.

After a dish is selected, the culinary application generates the recipe for the dish. The recipe can include two sets of instructions for preparing the selected dish. For example, a first set of instructions can include information regarding the activities to be performed by a first user of a specified age range, e.g., a parent, to prepare the dish and a second set of instructions can include information regarding the activities to be performed by a second user, e.g., a child, in preparing the dish. In some embodiments, the second set of instructions can include instructions for guiding the parent on how to safely involve the child in the cooking process. The first set of instructions and the second set of instructions can be mutually exclusive. In some embodiments, by generating two different sets of instructions and having different activities for both the parent and child and by facilitating the parent to guide the child in the cooking process, the culinary application enables the parent and the child to engage with each other.

In the discovery process of the recipes, the culinary application can also present certain trivia related to the recipe. The trivia can be in various subjects, e.g., math, science, geography, social awareness. The trivia can include information such as benefits of a particular ingredient in the recipe, information about a country where a dish prepared using the recipe is popular, math involved in measurements of ingredients, awareness about social causes in the particular country, etc. In some embodiments, the trivia can be presented in a format that is interesting to the child, e.g., as a quiz, an image, a video, animation. In some embodiments, the recipe is presented after the child has viewed at least some of the trivia. For example, the culinary application can display the recipe only after the child answers a quiz. In some embodiments, ensuring that the recipe is generated after the user has answered a quiz facilitates in ensuring that the child is also learning about various topics while learning cooking. The trivia can be presented at various stages, e.g., while the child is selecting the parameters for discovering the recipes and after the recipe is generated.

Environment

FIG. 1 is a block diagram illustrating an environment 100 in which a culinary application can be implemented. The environment 100 includes a server computing device ("server") 105 that can be used to implement a culinary application 145 using which consumers can search for recipes. The terms "user" and "consumer" which refers to a user using the culinary game application can be used interchangeably. Note that the terms "big chef" and "little chef" as used herein refer to users of different age groups. For example, a big chef can refer to a user of an adult age group, e.g., 13 years and above, who can safely guide the "little chef" in the cooking process, and a little chef can refer to a user of a little chef age group, e.g., 4-12 years, who can perform the activities in the cooking process under the guidance of the big chef. In one example, a big chef can be a parent and a little chef can be a child of the parent. Further, note that unless specified otherwise the user 115 can refer to a big chef 115a and/or a little chef 115b.

The culinary application 145 can facilitate children to search for recipes, learn various aspects while searching recipes, and indulge in preparing a meal with their parents using the generated recipe. The culinary application 145 can be implemented in various formats. For example, the culinary application 145 can be implemented as an online website, e.g., executing on the server 105, that can be accessed using a browser application on a client computing device ("client") 110. In another example, the culinary application 145 can be implemented as a downloadable application ("app") that can be downloaded to and installed on the client 110. In some embodiments, a portion of the culinary application 145 can be implemented on the server 105 and another portion on the client 110. The client 110 can include various devices such as a tablet, a laptop, a smartphone, a desktop, or any other computing device that is capable of accessing the culinary application 145.

The server 105 can obtain information, including recipes, trivia, user profile information of the user from various sources, e.g., third party systems 150. The server 105 can obtain recipes from third party systems 150, e.g., of third parties that have partnered with an entity associated with the culinary application 145 and/or from users of the culinary application 145. The server 105 can also share recipes with the third party systems 150. The server 105 can facilitate the users to share their recipes with other users of the culinary application 145 and/or users in a social networking application. The server 105 can interact with the third party systems 150 to obtain trivia, e.g., trivia related to a recipe. The server 105 can also provide an application programming interface (API) using which a third party can integrate the culinary application 145 with their application. For example, using the API, a third party culinary website can display some of the recipes associated with the culinary application 145 to their users. The server 105 can also facilitate a social networking application to integrate the culinary application 145 using the API. The server 105 can interact with the third party systems 150, such as charitable organizations, to contribute to a social cause, e.g., to donate money to a charitable organization. The server 105 can store information, e.g., recipes, trivia, user profile information of the user at a storage system 155. In some embodiments, the recipes and/or the trivia can also be uploaded to the server 105 by a user associated with the server 105, e.g., an administrator 140 of the server 105. In some embodiments, the server 105 stores the recipe and the trivia in a specific format, e.g., as a recipe template (which is described at least with reference to FIGS. 2A-2C below).

The server 105 enables the user 115 to search for recipes in an interactive way while learning about various other topics, including math, science, geography and social responsibility. For example, the server 105 generates not only a recipe 125, but also presents trivia 130 that can include information on various topics, e.g., nutritional information, information about places, information about culture where the recipe is popular, math involved in measurements.

The user 115 can specify a set of parameters 120 based on which the server 105 can search for recipes. For example, the set of parameters 120 can include a country whose dishes the user 115 is interested in, ingredients of the dish the user 115 is interested in, a calories range of the dishes the user 115 is interested in, nutritional information, a favorite vegetable and/or fruit, a type of occasion, a cooking duration, a type of ingredient, a type of diet, equipment that may be required, an ethnic group, a particular culture. The user 115 can also select a particular dish the user is interested in. In some embodiments, the server 105 generates a GUI on the client 110 using which the user 115 can interact with the culinary application 145.

The server 105 enables the user 115, e.g., the big chef 115a or the little chef 115b, to search for the recipes in an interactive way. In one example, the interactive process can include the server 105 generating an image of a vegetable or a fruit in the GUI on the client 110, prompting the little chef 115b to identify the vegetable or fruit, and presenting, upon identification of the vegetable or the fruit, one or more recipes including the vegetable or the fruit. In another example, the server 105 can prompt the user 115 to specify the set of parameters 120, e.g., by inputting text into the game application or selecting them from various parameters presented in the GUI. In yet another example, the server 105 can prompt the user 115 to specify a place like a country or city of user's interest and then present one or more recipes that are popular in the country or the city. Various other interactions may be included to prompt the user 115 to express their interests. In the process of so prompting, the culinary application 145 can stimulate the thought process of the little chef 115b. FIGS. 3-13 illustrate example GUIs using which the user can input the set of parameters 120 and/or interact with the culinary application 145.

After the user 115 specifies the set of parameters 120, the server 105 searches various sources, e.g., the third party systems 150, the storage system 155, for the recipes based on the set of parameters 120. The server 105 retrieves a recipe 125 for the selected dish and transmits the recipe 125 to the client 110. The client 110 displays the recipe 125 in the GUI. In some embodiments, the recipe 125 includes two sets of instructions, e.g., a first set of instructions that includes information regarding activities to be performed by the big chef 115a in preparing the dish of the recipe 125 and a second set of instructions that includes information regarding activities to be performed by the little chef 115b in preparing the dish of the recipe 125. The two sets of instructions can be mutually exclusive, that is, the activities to be performed by the big chef 115a can be different from the activities to be performed by the little chef 115b. So, the culinary application 145 enables the big chef 115a and little chef 115b to engage with each other and have a fun interactive culinary experience.

In some embodiments, the server 105 also generates trivia 130 on one or more topics with the recipe 125. The trivia 130 can include educational information for the little chef 115b and/or the big chef 115a. The trivia 130 can include educative information that is related to the recipe 125. The educative information can be presented in various areas, including math, geography, science and social responsibility. For example, if the recipe 125 includes a particular vegetable such as a carrot, then the server 105 can generate trivia 130 such as "Carrot is good for your eyes." In another example, if a particular dish selected by the user 115, e.g., sushi, is popular in a particular country, e.g., Japan, then the server 105 can display trivia 130 about that country. The server 105 can retrieve trivia from one or more of the third party systems 150, e.g., Wikipedia, or from the storage system 155. The third party systems 150 can include any servers or systems accessible by the server 105 over a computer network, e.g., Internet, and that allow the server 105 to retrieve the information from them. In some embodiments, the administrator 140 can also upload trivia to the server 105.

The server 105 determines the content of the trivia 130 to be presented based on a target age group of the users. For example, for the big chef 115a, the trivia 130 can be more detailed and more specific, such as "Omega-3 fatty acid is able to stimulate a hormone called leptin, which helps the body's metabolism while regulating the body's weight and food intake." For a little chef, the same trivia can be presented as "This dish contains an Omega-3 fatty acid which helps in digestion." Further, the trivia 130 may be presented in a format that is interesting and attractive to the little chef 115b. For example, the trivia 130 can be presented in multimedia format such as text, an image, audio, video, animation, etc. Further, the server 105 can format the trivia 130 based on a target age group of the little chefs. For example, if the target age group is users of 4-6 years, the server 105 can present the trivia 130 using bright colors, animated pictures, videos, simple words, etc., that is attractive to and easily understandable by little chefs of that age.

In some embodiments, the server 105 can facilitate the user 115 to obtain additional information about the trivia 130. For example, the server 105 can include an information link with the trivia 130, using which the user 115 can obtain additional information about the aspect presented in the trivia 130. When the user 115 selects the information link, the server 105 can obtain the additional information from the third party systems 150 and/or the storage system 155 and display the additional information associated with trivia 130.

The trivia 130 can also be math related trivia. For example, the trivia 130 can be like "A gallon is 4 quarts. Each quart is 32 oz." This may be helpful in teaching the little chef about conversion of units. In some embodiments, the server 105 can also present trivia regarding social causes. For example, the trivia 130 can include information about helping other children who are not fortunate enough to have food on their plate every day. The trivia 130 can include a link for donating the money. When the user 115 selects the link, the user 115 is directed to a GUI within the culinary application 145 and/or a third party system 150 where the user 115 can donate money. The trivia 130 can also provide details about social cause events occurring in the neighborhood. In some embodiments, the server 105 determines the location of the user 115 in various ways, e.g., using data from a global positioning system (GPS) of the client 110, using information based on an Internet Protocol (IP) address of the client 110. After determining the location of the user 115, the server 105 can search the third party systems 150 or the storage system 155 for the social causes in the specified location. The trivia 130 facilitates the user 115 to donate time, e.g., in terms of volunteering, or money to a social cause. This can also help the little chef to become aware of their social responsibilities.

The server 105 can present various types of trivia 130 in various stages in the discovery process of the recipes. For example, some of the trivia 130 can be presented to the user 115 while the user 115 is searching for the recipes, some when the recipe 125 is generated, and some upon completing a particular step of the recipe 125. In some embodiments, the server 105 can present the recipe 125 to the user 115 after the user 115 has viewed at least a portion of the trivia 130. For example, the server 105 can generate portion of trivia 130 as a quiz, and the server can show the recipe 125 to the user 115 or proceed to the next stage in the discovery process only if the user responds to the quiz. In some embodiments, the trivia 130 can include a link for proceeding to a next stage in the discovery process. The user 115 can select the link after reading the trivia 130 and the server 105 can then proceed to the next stage in the discovery process. By having at least a portion of the trivia 130 displayed to the user 115 before generating the recipe 125 the server 105 can ensure that the likelihood of the little chef 115b reading the trivia 130 is higher than when the trivia 130 is presented after the recipe 125 is presented.

By showing the educational information along with interactive searching process, not only the little chef 115b can have fun culinary experience but can also learn about various topics.

In some embodiments, the culinary application 145 can be integrated with a shopping application, e.g., one of the third party systems 150, using which the user 115 can shop online for various products, including ingredients for a particular recipe. For example, the user 115 can specify in the culinary application 145 if certain ingredients of a particular dish the user 115 is requesting the recipe for is unavailable and the server 105 facilitates generating an online order for purchasing those ingredients from the shopping application.

In some embodiments, the culinary application 145 can be integrated with social networking applications, such as Facebook of Menlo Park, Calif.; Twitter of San Francisco, Calif.; Google+ of Google, Mountain View, Calif., etc. The users, e.g., user 115, may share the recipes from the culinary application 145 with other users using the social networking applications. The server 105 also facilitates the user 115 to post pictures, videos, of the dish prepared using the recipe 125 on the social networking applications. The user 115 may also invite other users, e.g., their friends and families, from their social networking applications to use the culinary application 145.

In some embodiments, the culinary application 145 can assign a score, e.g., loyalty points, to the user 115, for performing certain activities. For example, the culinary application 145 can provide loyalty points for any of the following: creating a profile with the culinary application 145, answering the questions posted by the culinary application 145 as part of the trivia 130, cooking a meal using the recipe 125, posting an image of the meal cooked using the recipe to a social networking application, posting a recipe to the culinary application 145, buying products or services from the culinary application 145. Different number of loyalty points can be awarded for different types of activities.

Each loyalty point can have an associated financial value. The user 115 may exchange the loyalty points for any of: cash, merchandise, ingredients, membership to the culinary application 145. In some embodiments, the user 115 can use the loyalty points to donate money for a social cause. For example, the user 115 can donate points to various charitable organizations.

FIGS. 2A, 2B and 2C, collectively referred to as FIG. 2, is an example template 200 of a recipe and trivia that can be presented using the culinary application of FIG. 1, consistent with various embodiments. In some embodiments, the recipe and trivia in the example 200 are similar to the recipe 125 and the trivia 130 of FIG. 1. The example template 200 includes a recipe for a dessert "Quince Paste Tart" that is popular in the country "Argentina." The recipe in the template example 200 includes two sets of instructions. For example, FIG. 2B illustrates a first set of instructions 205 that includes information regarding activities to be performed by the big chef 115a and a second set of instructions 210 that includes information regarding activities to be performed by the little chef 115b. The example template 200 also includes trivia on various topics. For example, the "Fun Fact" trivia in FIG. 2A includes information on the country Argentina, the "Ingredient spotlight" includes information on the ingredients of the dessert, and trivia 250 in FIG. 2C illustrates various other trivia that can be presented with the recipe.

In some embodiments, the server 105 can generate templates, such as the example template 200, as and when the server 105 receives content, e.g., recipe and/or the trivia from various sources, e.g., user 115, the administrator 140, third party systems 150. For example, when the administrator 140 inputs a recipe and/or the trivia to the server 105, the server 105 can generate such a template based on the content input by the administrator 140. In some embodiments, the server 105 can have the administrator 140 input the content in the above template. For example, the culinary application 145 can include a content input GUI which can require the administrator 140 to input the content in the above format of the example template 200. Some fields in the content input GUI may be mandatory, which requires an input from the administrator 140, and some fields may not be mandatory. For such non-mandatory fields, the server 105 can search for the information from various third party systems 150 and then add the obtained information to the template. For example, some of the trivia fields, e.g., information regarding where the tools required for preparing the dish are available from purchase, can be non-mandatory and the server 105 can obtain such information from third party systems 150, e.g., crawl the Internet to obtain the information. The server 105 can also obtain recipes from the third party systems 150 and generate templates, e.g., in the format of example template 200, to store the retrieved recipes. The server 105 can store the templates in the storage system 155. In some embodiments, the server 105 uses the templates to present the recipe and the trivia in various GUIs as described below.

While the example template 200 illustrates storing some content, e.g., trivia and ingredient information, with the recipe in a single template, in some embodiments, the server 105 can also store some of the content independent of the recipe. For example, trivia such as information regarding a country, which can be presented with more than one recipe, can be stored separately. Also, since in some embodiments, some of the trivia 130 can be presented to the user 115 before the user 115 selects a dish, the server 105 can store some of the trivia independent of the example template 200.

The following figures and paragraphs describe various GUIs of the culinary application 145 using which the user 115 can discover recipes. In some embodiments, each of the GUIs in FIGS. 3-13 represents a different stage of the recipe discovery process.

Figure 3A:
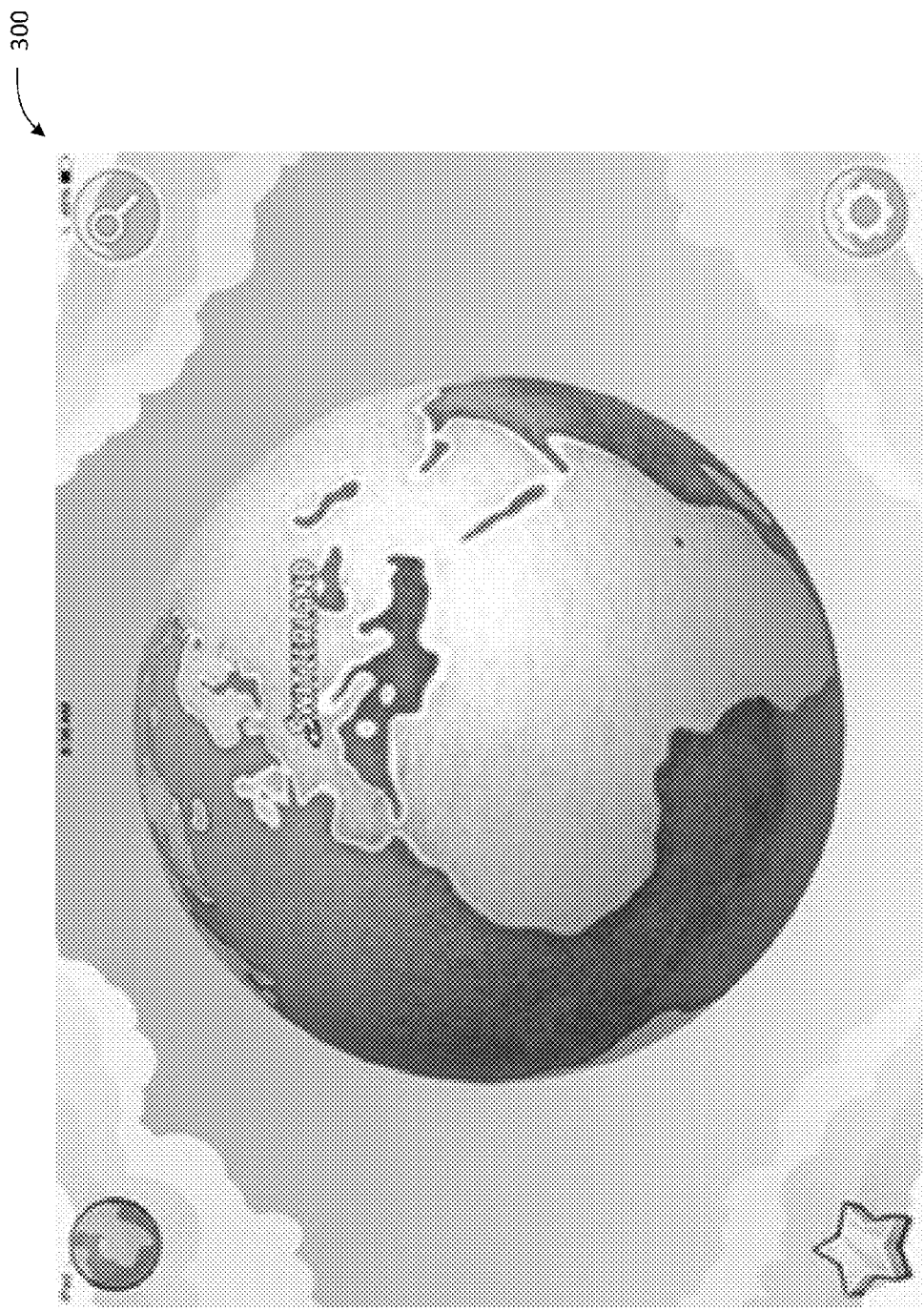
FIG. 3A is an example graphical user interface (GUI) using which a user can specify a country of the dish the user is interested in, consistent with various embodiments.

FIG. 3A is an example of a first GUI 300 using which a user can specify a country of the dish the user is interested in, consistent with various embodiments. In some embodiments, the first GUI 300 displays a three dimensional rotating globe with a world map on it. The user 115 can specify a country whose dishes the user 115 is interested in by selecting a particular country from the globe. The first GUI 300 can enable the user to select a country in various other ways. For example, the first GUI 300 can display a list of country names and the user 115 can select one of the countries. In another example, the first GUI 300 can display flags of various countries, and the user 115 can select a country by selecting one of the flags. Further, note that the first GUI 300 can also present other locations, such as cities, states.

Figure 3B:
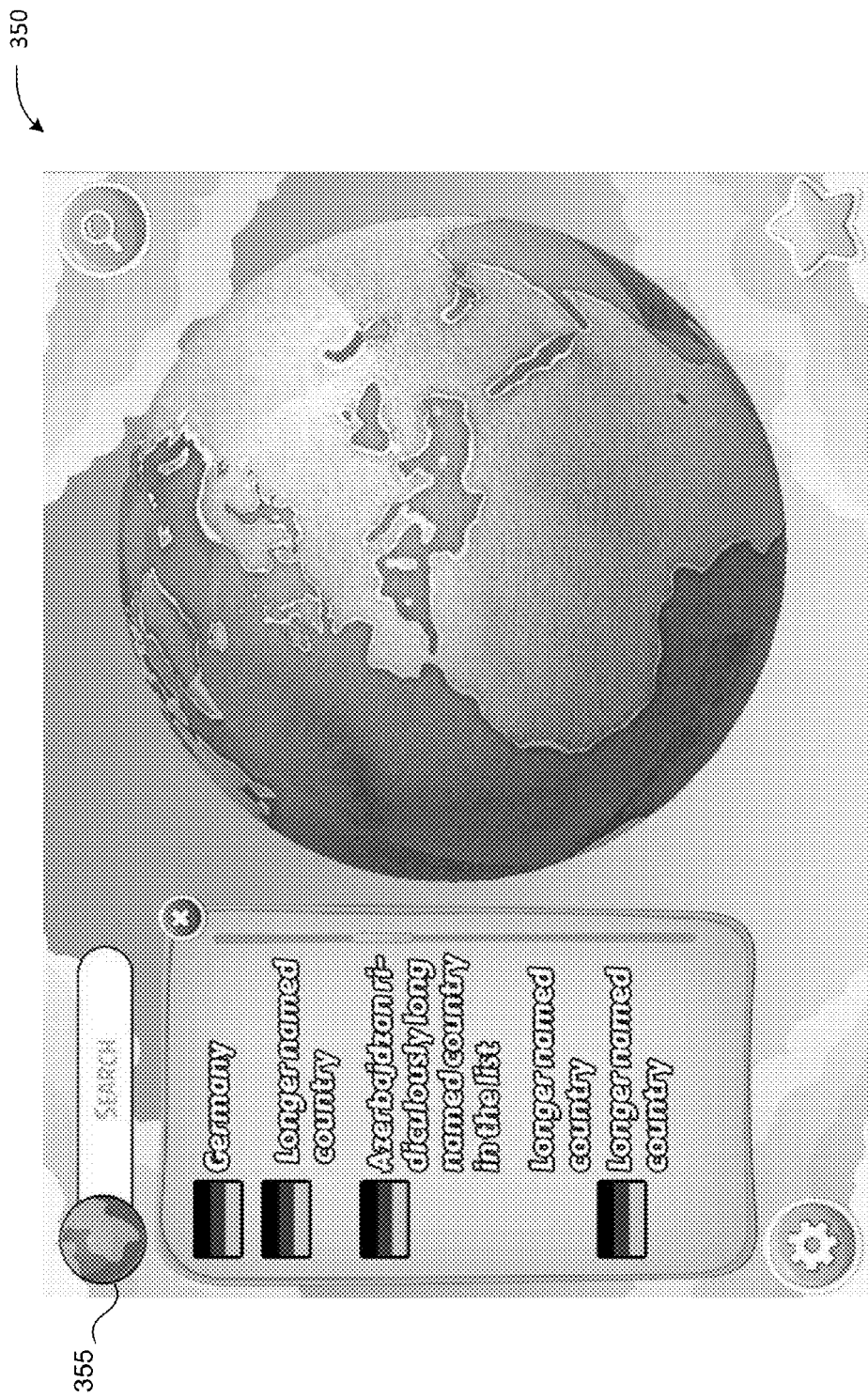
FIG. 3B is another example GUI using which a user can specify a country of the dish the user is interested in, consistent with various embodiments.

FIG. 3B is another example GUI 350 using which a user can specify a country of the dish the user is interested in, consistent with various embodiments. The GUI 350 includes a search bar 355 using which the user 115 can search for a country by the name of the country. In some embodiments, the search bar 355 can be an universal search bar for the culinary application 145 which can be used to search for various content, e.g., recipes, ingredients, across the culinary application 145.

Figure 4A:
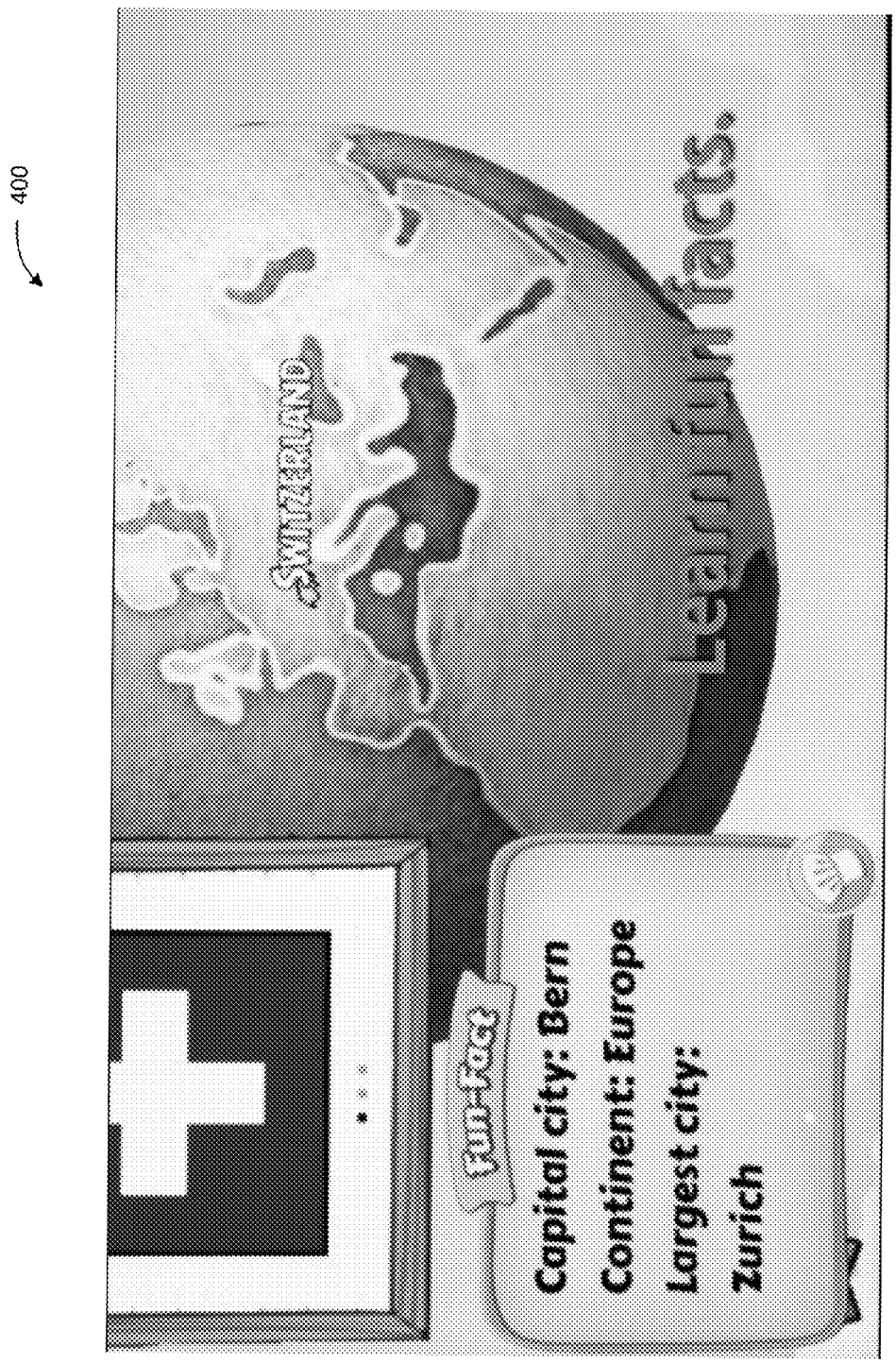
FIGS. 4A and 4B are examples of GUIs for displaying trivia related to the country selected in the GUI of FIG. 3, consistent with various embodiments.
Figure 4B:
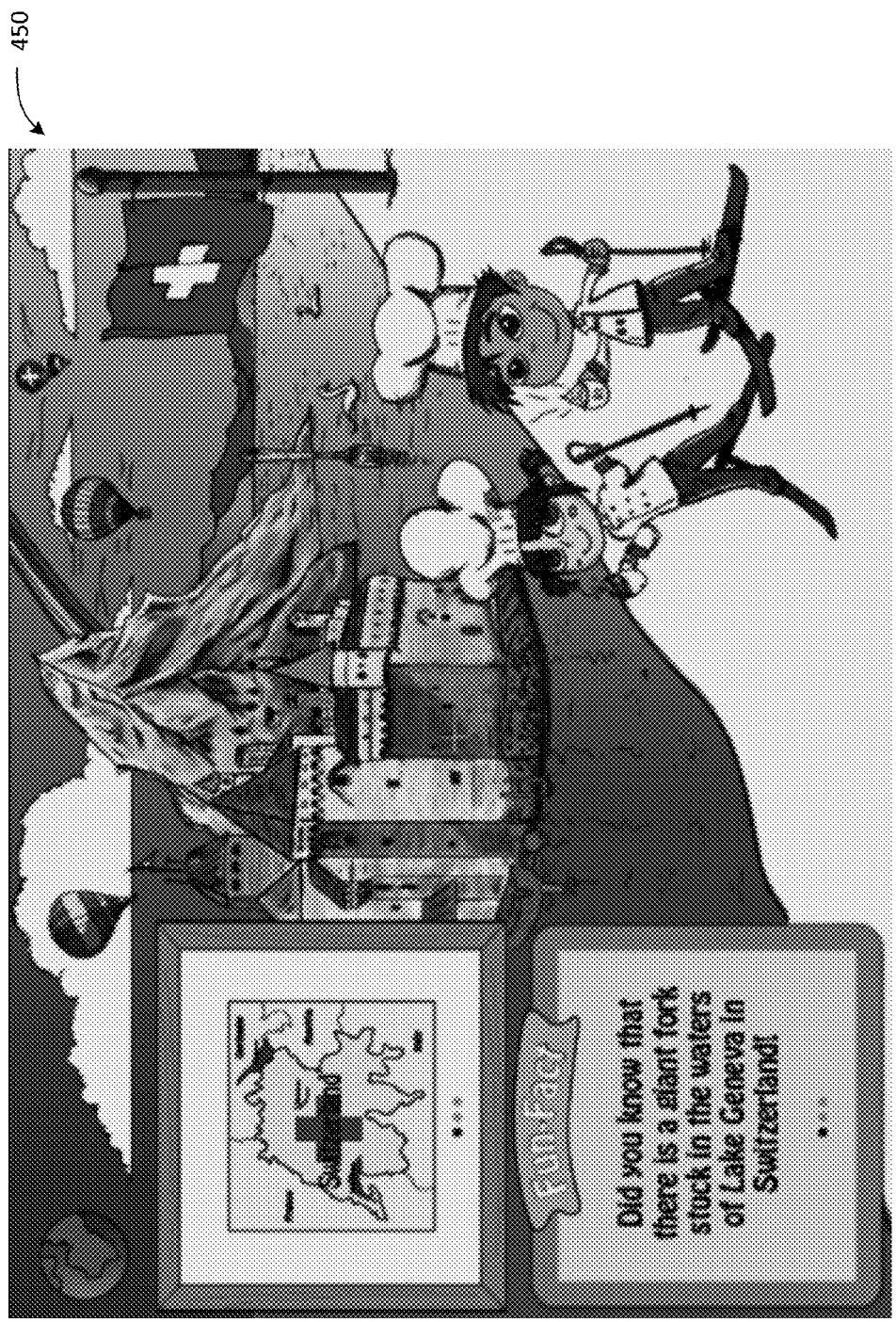

FIGS. 4A and 4B are examples of a second GUI 400 and a third GUI 450 for displaying trivia related to the country selected in the first GUI 300 of FIG. 3, consistent with various embodiments. After the user 115 selects the country in the first GUI 300 the server 105 can generate the second GUI 400 and/or the third GUI 450 for displaying trivia related to the selected country.

Figure 5A:
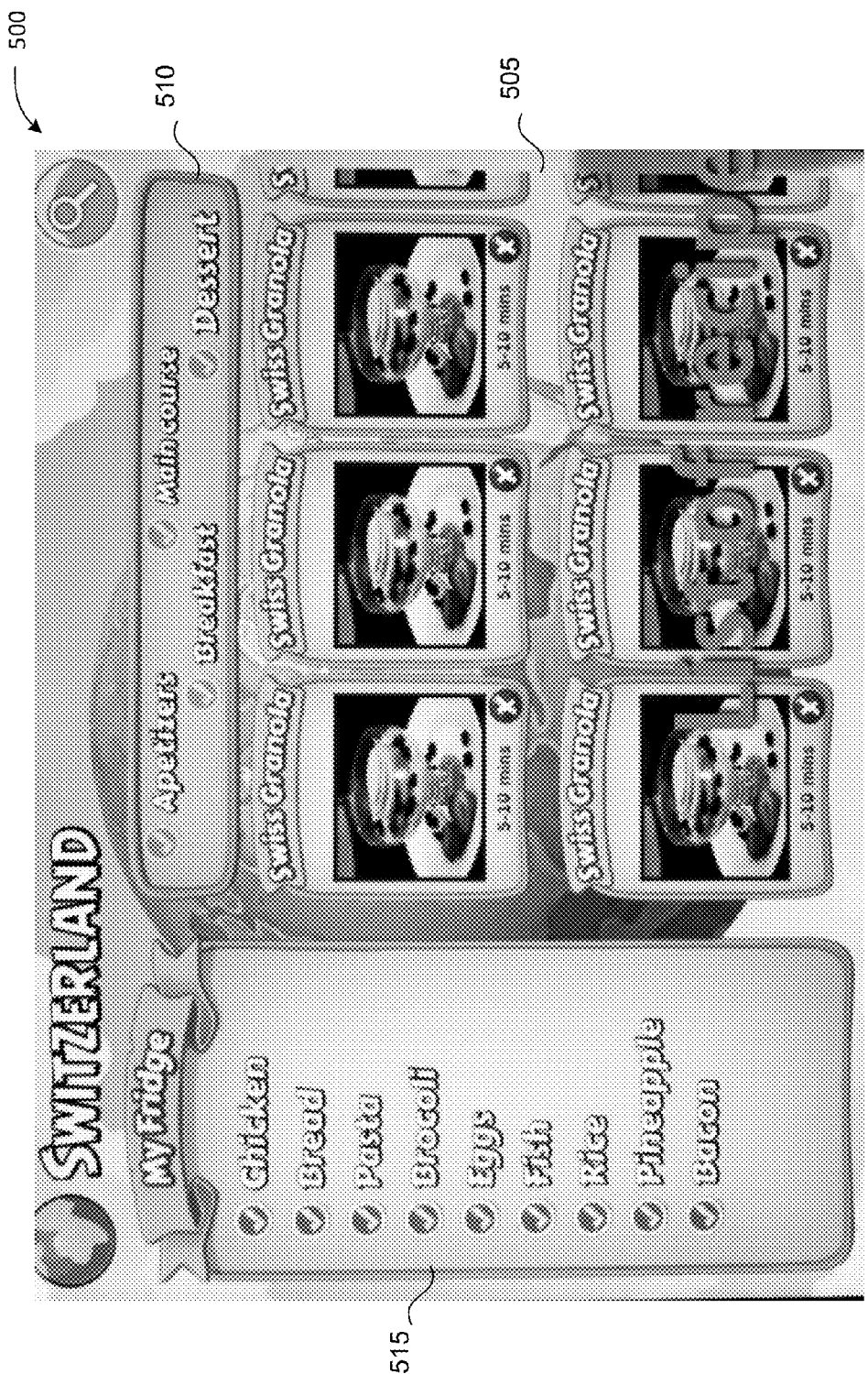
FIG. 5A is an example GUI for displaying a list of dishes of the country selected in FIG. 3, consistent with various embodiments.

FIG. 5A is an example of a fourth GUI 500 for displaying a list of dishes of the country selected in FIG. 3, consistent with various embodiments. The fourth GUI 500 displays a list of dishes 505 of the country selected in FIG. 3. The user 115 can select one of the dishes from the list of dishes 505. The user 115 can also filter the list of dishes 505 based on the type of the meal, e.g., appetizer, breakfast, main course, the user 115 wants to cook. The user 115 can filter the list of dishes 505 based on the meal type using the tool bar 510. The user 115 can also filter the list of dishes 505 based on user preferred ingredients. The user 115 can specify the preferred ingredients using in the side bar 515. In some embodiments, the user can specify the list of ingredients the user 115 has in his/her fridge in the side bar 515 and the server 105 filters the list of dishes 505 to retrieve only the dishes that can be made using the any of the list of ingredients. The user 115 can then select a particular dish from the list of dishes 505.

Figure 5B:
FIG. 5B is an example GUI for specifying a list of ingredients, consistent with various embodiments.

FIG. 5B is an example GUI 550 for specifying a list of ingredients, consistent with various embodiments. The user 115 can also specify the ingredients that the user 115 is not interested in, e.g., ingredients the user 115 is allergic to using the GUI 550. In some embodiments, information regarding the ingredients the user 115 is allergic to can be stored as part of the user preferences in the culinary application 145. The server 105 ensures that the dishes including any of the ingredients the user 115 is allergic to is not presented to the user 115.

Figure 6:
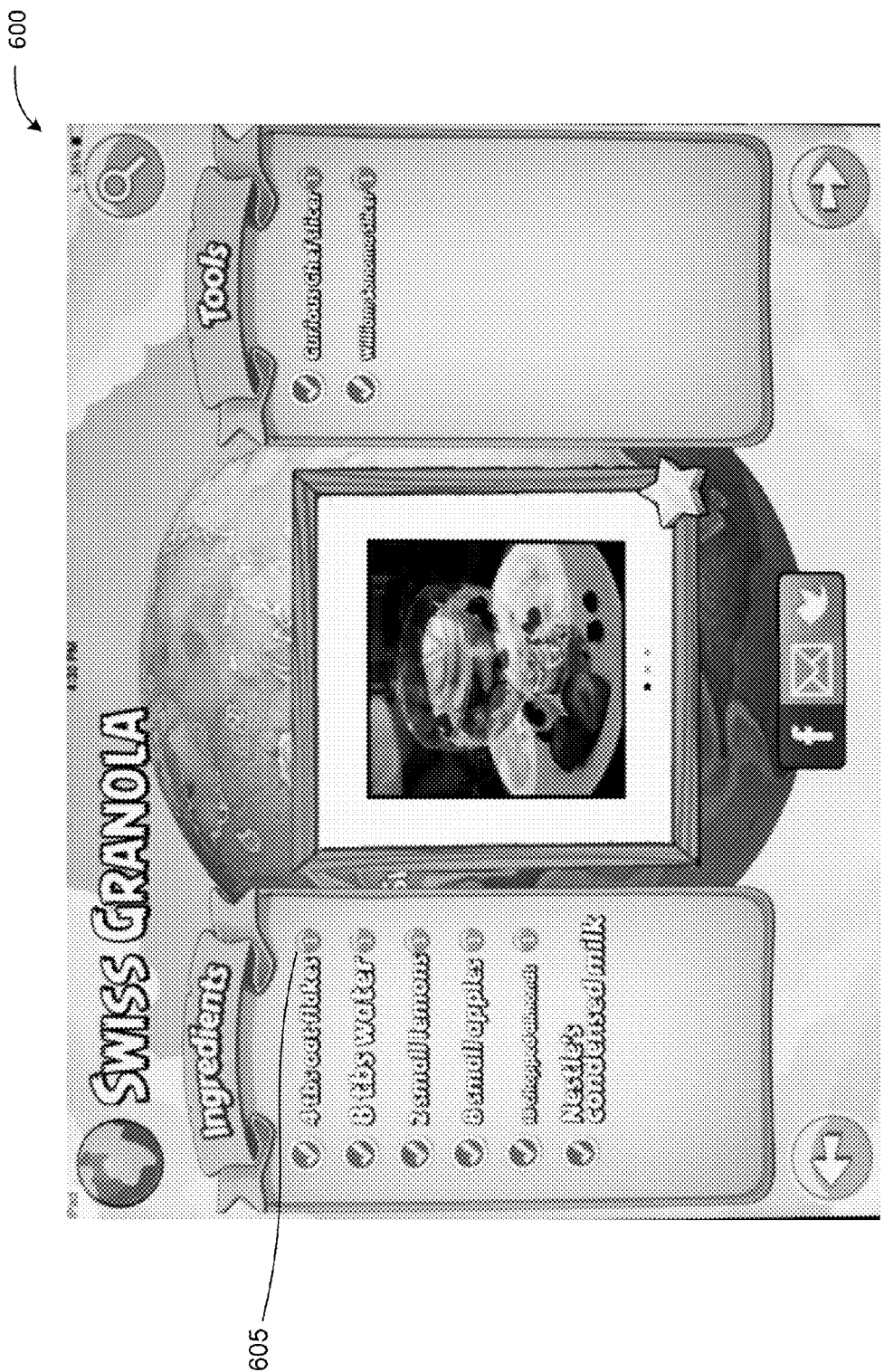
FIG. 6 is an example GUI for displaying a user selected dish and ingredients of the dish, consistent with various embodiments.
Figure 7:
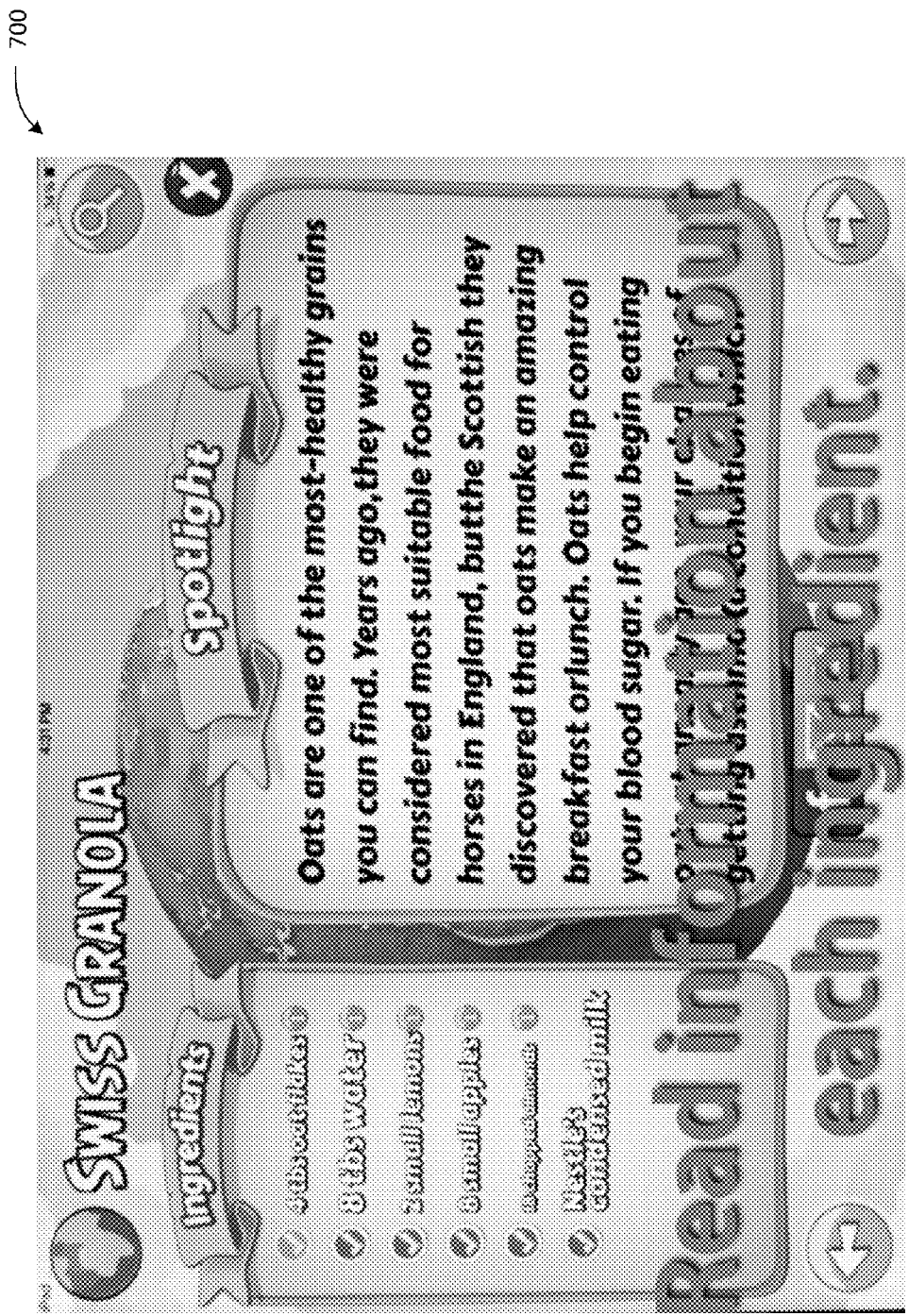
FIG. 7 is an example GUI for displaying information associated with an ingredient of a dish, consistent with various embodiments.

FIG. 6 is an example of a fifth GUI 600 for displaying a user selected dish and ingredients of the dish, consistent with various embodiments. The fifth GUI 600 displays the dish the user 115 selected in the fourth GUI 500 and the ingredients of the dish. The fifth GUI 600 can display an image or a video of the dish. In some embodiments, the fifth GUI 600 can facilitate the user 115 to obtain additional information e.g., trivia 130, about the each of the ingredients of the dish. For example, the fifth GUI can generate a link 605 for an ingredient of the dish. The user 115 can select the link 605 and view the additional information regarding the ingredient, e.g., as illustrated in FIG. 7. FIG. 7 is an example of a sixth GUI 700 for displaying information associated with an ingredient of a dish, consistent with various embodiments. The sixth GUI 700 displays information regarding the oat flakes. In some embodiments, the server 105 can use the templates, e.g., example template 200 of FIG. 2, of a recipe, which contains information regarding the ingredients of the dish, additional information regarding the ingredients, trivia, recipe, etc.

Returning to FIG. 6, the fifth GUI 600 can also display information regarding the necessary tools for preparing the dish. In some embodiments, the fifth GUI 600 can also include a link to a website of a third party system 150, e.g., an online merchant, where the user 115 can purchase the tools from.

Figure 8:
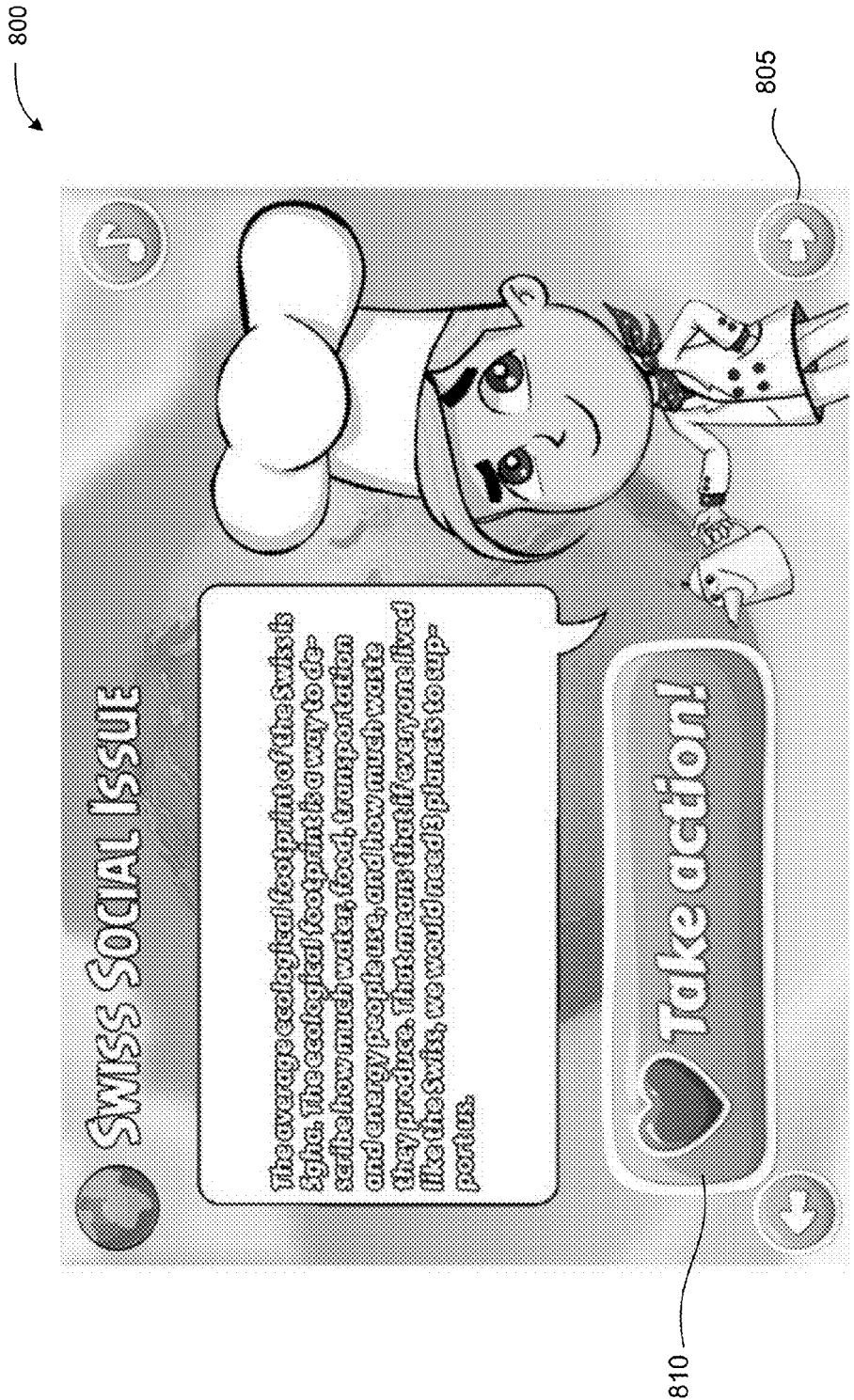
FIG. 8 is an example GUI for displaying trivia related to the selected dish, consistent with various embodiments.

FIG. 8 is an example of a seventh GUI 800 for displaying trivia related to the selected dish, consistent with various embodiments. In some embodiments, the seventh GUI 800 displays information regarding a social issue associated with a country, e.g., the country of the dish the user selected in FIG. 3. In some embodiments, the server 105 can use the templates, e.g., example template 200 of FIG. 2, of a recipe, which contains trivia regarding the country of the dish, social issues in the country, etc., to present the trivia in the seventh GUI 800.

Note that while the server 105 may not show some trivia unless requested by the user 115 (e.g., information about ingredients as shown in FIG. 7, where the user 115 can view them by selecting a link such as link 605), the server 105 may show some trivia, e.g., social issue trivia as displayed in seventh GUI 800, regardless of whether the user has requested. The user 115 may have to indicate to the server 105 that the user has read the trivia, e.g., by selecting a next link 805 or "take action" link 810 to proceed to a next stage in recipe discovery process. In some embodiments, selecting the next link 805 causes the user 115 to proceed to a next stage of the discovery process, e.g., generation of recipe, and selecting the take action link 810 causes the user to proceed to a GUI where the user 115 can contribute, e.g., register for volunteering, to the social issue. By not proceeding to the next stage of the recipe discovery process until the user 115, e.g., little chef 115b, acknowledges the social issue, the culinary application 145 can ensure that the little chef 115b has read about and is aware of the social issue. The user 115 can proceed to the next stage of the recipe discovery process by selecting the next link 805.

Figure 9:
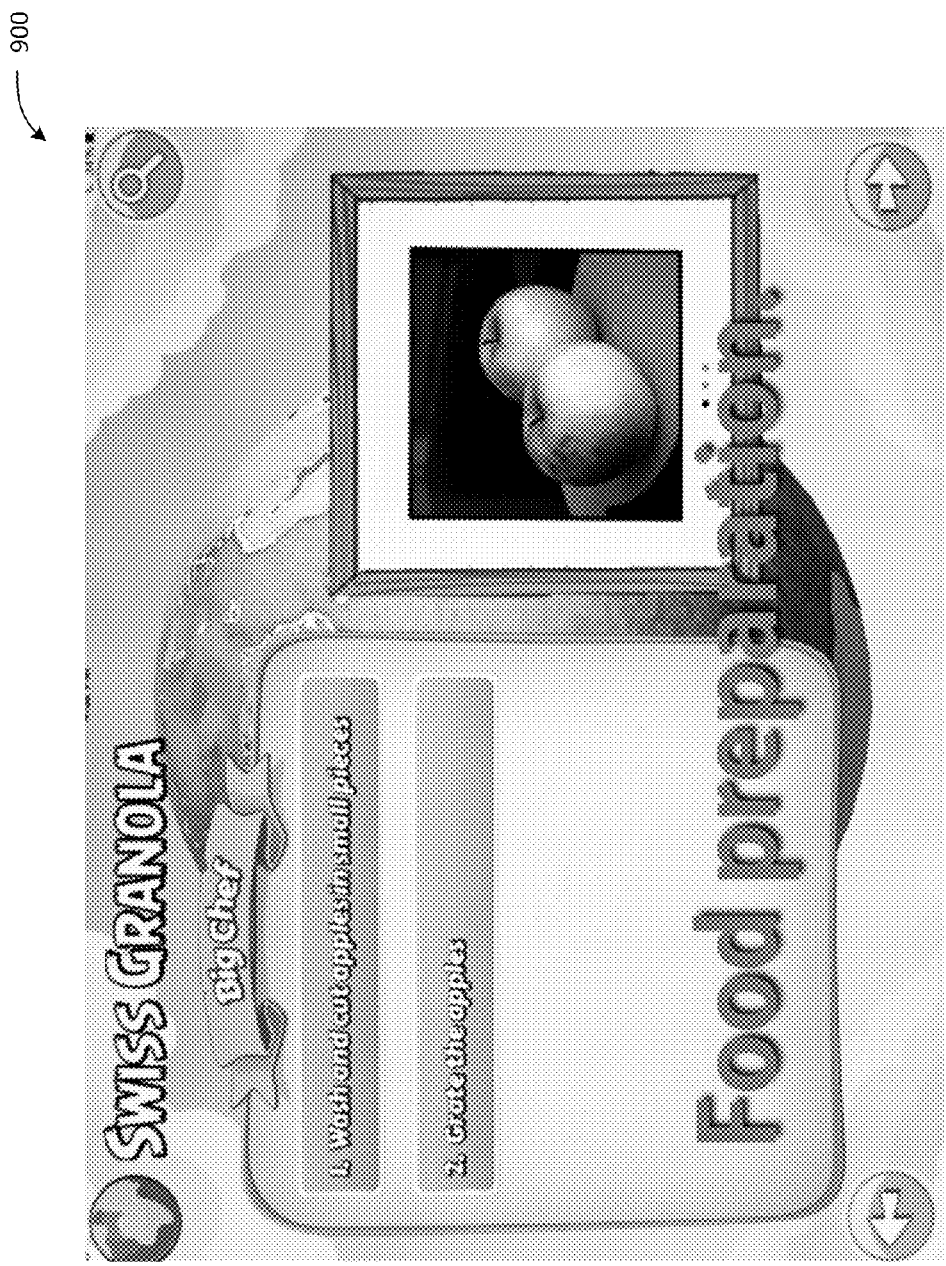
FIG. 9 is an example GUI for displaying a first set of instructions of the recipe, which includes information regarding activities to be performed by a big chef, consistent with various embodiments.
Figure 10:
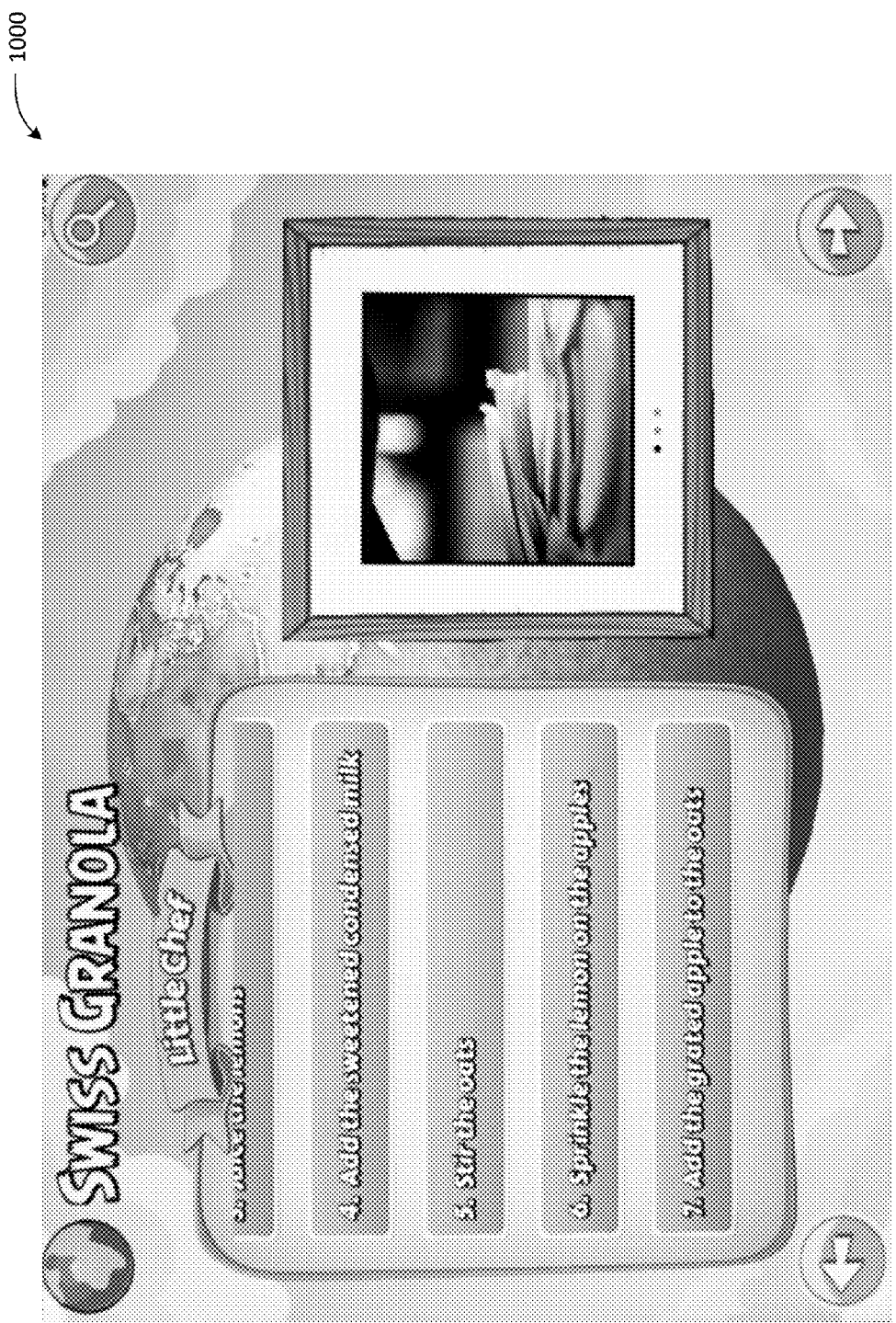
FIG. 10 is an example GUI for displaying a second set of instructions of the recipe, which includes information regarding activities to be performed by a little chef under the supervision of the big chef.

FIGS. 9 and 10 are examples of an eighth GUI 900 and a ninth GUI 1000 for displaying the recipe of a user selected dish, consistent with various embodiments. In some embodiments, the user 115 can select a dish as illustrated in FIG. 5. In some embodiments, the recipe of FIGS. 9 and 10 is similar to the recipe 125 of FIG. 1. The eighth GUI 900 of FIG. 9 displays a first set of instructions of the recipe, which includes information regarding activities to be performed by a big chef 115a. The ninth GUI 1000 of FIG. 10 displays a second set of instructions of the recipe, which includes information regarding activities to be performed by the little chef 115b under the supervision of the big chef 115a. In some embodiments, the first set of instructions and the second set of instructions are mutually exclusive. In some embodiments, the server 105 can use the templates, e.g., example template 200 of FIG. 2, of a recipe, which contains the sets of instructions for both big chef 115a and the little chef 115b for preparing the dish, to present the instructions in the eighth GUI 900 and the ninth GUI 1000.

Figure 11:
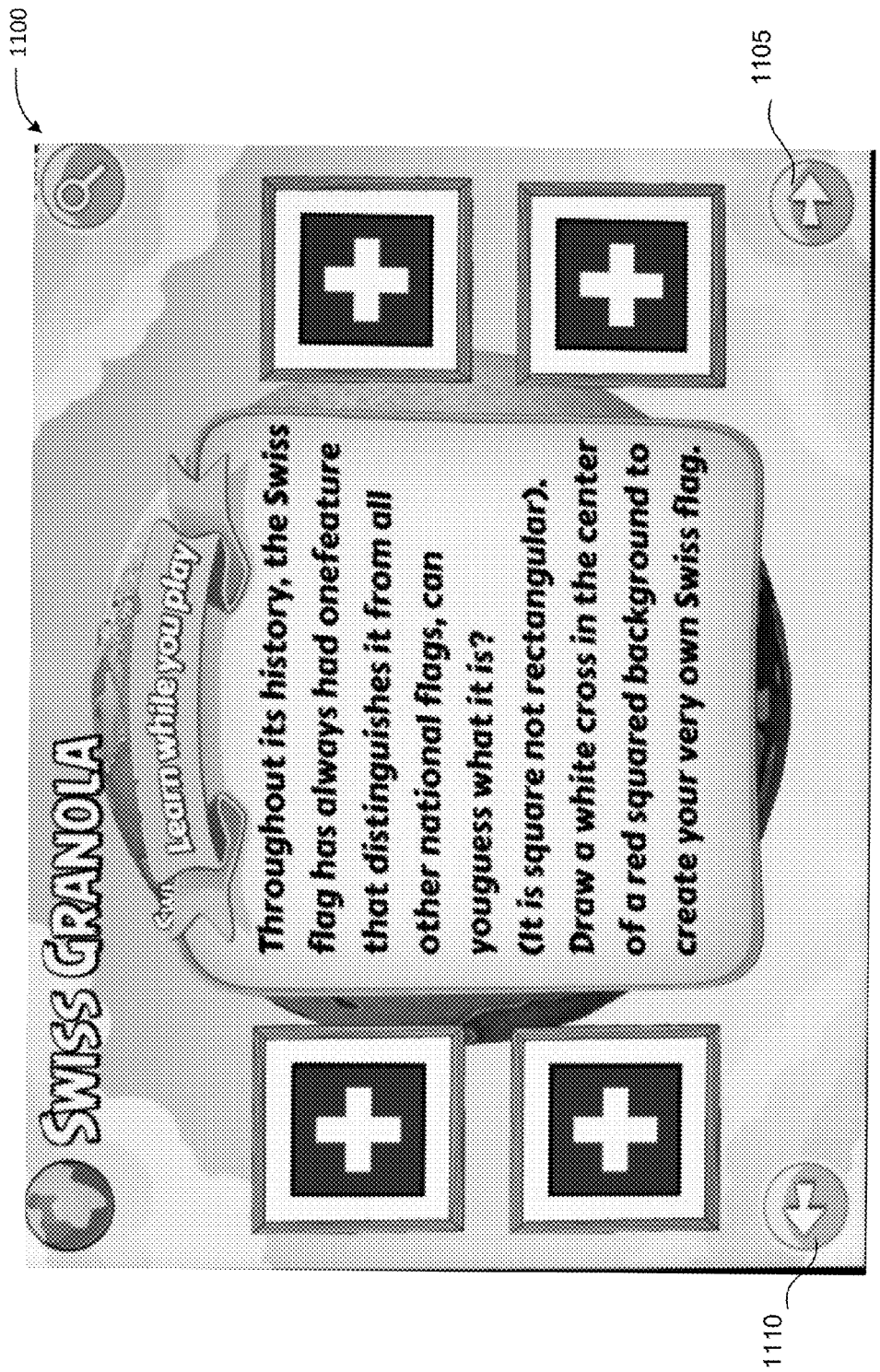
FIG. 11 is an example of a GUI for displaying trivia related to the recipe of a user selected dish, consistent with various embodiments.

FIG. 11 is an example of a tenth GUI 1100 for displaying trivia related to the recipe of a user selected dish, consistent with various embodiments. In some embodiments, the server 105 can generate some trivia that the user 115 can view while preparing the dish of the recipe. For example, the user 115 can read the trivia when the user 115 has to wait in between the steps of the recipe. The tenth GUI 1100 displays information about the country of the dish. After reading the trivia in the tenth GUI 1100, the user 115 can proceed to the next stage by selecting next link 1105, or go back to previous stage, e.g., ninth GUI 1000, to complete the remaining steps of the recipe by selecting previous link 1110.

Figure 12:
FIG. 12 is an example of a GUI for displaying presentation instructions of the dish, consistent with various embodiments.

FIG. 12 is an example of a eleventh GUI 1200 for displaying presentation instructions of a dish prepared using the recipe, consistent with various embodiments. The eleventh GUI 1200 can display the presentation instructions of the recipe, which can include instructions for preparing the dish for serving. In some embodiments, the presentation instructions can either be performed by the big chef 115a or the little chef 115b depending on the complexity of the presentation instructions and the age of the little chef 115b.

Note that the sequence of the GUIs illustrated in FIGS. 3-12 is just an example sequence. The server 105 can generate the GUIs in a sequence different from the above illustrated sequence. Further, the order in which the user 115 specifies the parameters for selecting the dish in FIGS. 3-12 is also an example. The server 105 can generate the GUIs in a different sequence, which can require the user 115 to specify the parameters in a different order. For example, instead of specifying the country first and then the ingredients and the type of the meal, the server can generate the GUIs in such a way that the user 115 can specify the type of the meal first, then the ingredients and then the country. The user 115 can share content, e.g., recipe, with other users, e.g., friends of the user 115 in one or more social networking applications, using the links 1205.

Figure 13:
FIG. 13 is an example list of features of the culinary application of FIG. 1, consistent with various embodiments.

FIG. 13 is an example list of features of the culinary application 145 of FIG. 1, consistent with various embodiments. The culinary application 145 facilitates the user 115 to create user profiles. The user 115 can provide various user preferences as part of the user profile, which the server 105 can use in discovering recipes, presenting trivia, changing the look and feel of the GUI to suit the age-range of the user 115, etc. The culinary application 145 provides educational value to the user 115. For example, the culinary application 145 presents trivia on various topics, including math, science, geography, etc. The culinary application 145 can also facilitate the children to become aware of their social responsibilities.

The culinary application 145 can stimulate curiosity or the thought process of a little chef 115b, e.g., by quizzing the little chef to identify vegetables, fruits, places, etc. The culinary application 145 can also facilitate awareness of various cultures, for example, by presenting trivia related to a particular culture of a country of the selected recipe. The parents and children are provided incentives to engage in cooking a healthy meal. The culinary application 145 will facilitate the family in spending quality time together and also provide the little chef a fun experience of cooking a healthy meal.

Figure 14:
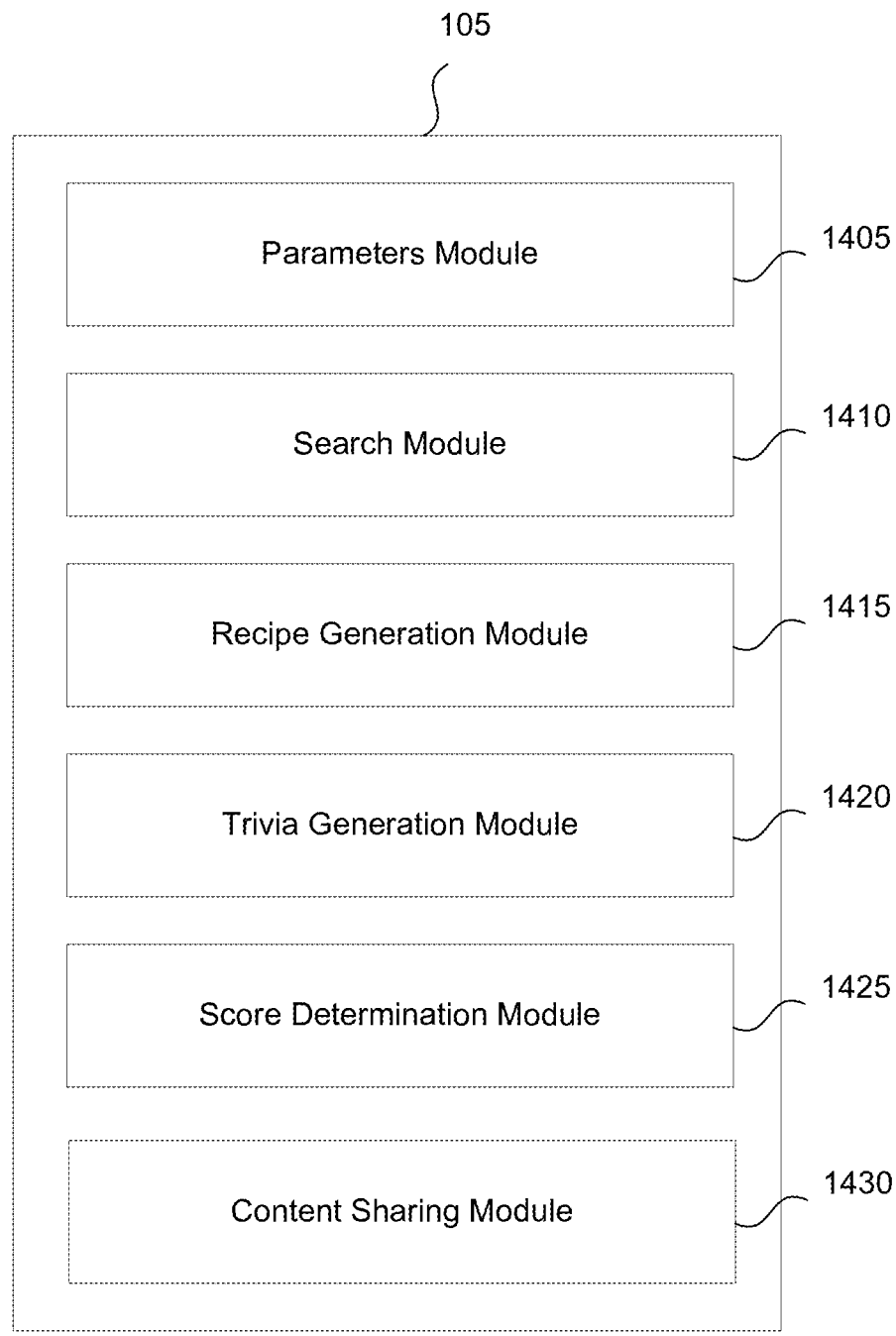
FIG. 14 is a block diagram of the server of FIG. 1, consistent with various embodiments.

FIG. 14 is a block diagram of the server of FIG. 1, consistent with various embodiments. In some embodiments, the server 105 implements at least a portion of the culinary application 145 using the modules 1405-1430. The server 105 includes a parameters module 1405 that can output a number of parameters to the user 115 based on which the recipes can be discovered, and receive a user selection of one or more of the parameters, e.g., set of parameters 120. The parameters module 1405 outputs the parameters in a GUI, e.g., first GUI 300, at the client 110. In some embodiments, the parameters module 1405 can present the parameters at least as described with reference to the foregoing figures.

The server 105 includes a search module 1410 that can search, e.g., the storage system 155, for dishes that satisfy the user specified parameters and the present a set of dishes to the user 115 in the GUI at the client 110. The search module 1410 can receive a user selection of a dish from the number of dishes for which the recipe, e.g., recipe 125, is to be generated. The search module 1410 can also search for trivia, e.g., trivia 130, that is to be displayed with the recipe generated for the dish. In some embodiments, the search module 1410 can search at the third party systems 150 and/or the storage system 155 for retrieving the recipes and the trivia.

The server 105 includes a recipe generation module 1415 that generates a recipe, e.g., recipe 125, for the user selected dish in the GUI at the client 110. In some embodiments, the recipe generation module 1415 generates the recipe as described at least with reference to FIG. 1 and FIGS. 9, 10 and 12.

The server 105 includes a trivia generation module 1420 that generates a trivia related to the recipe, e.g., trivia 130, in the GUI at the client 110. In some embodiments, the trivia generation module 1420 generates the trivia as described at least with reference to FIG. 1 and FIGS. 4A, 4B, 6-8 and 11. In some embodiments, the recipe generation module 1415 and/or the trivia generation module 1415 can generate recipe templates, e.g., example template 200, to store the recipes and trivia received from various sources, and can use the templates to generate the recipes and trivia in the GUI at the client 110.

The server 105 includes a score determination module 1425 that can be used to determine a score to be assigned to a user, e.g., user 115, for various activities performed by the user using the culinary application 145. In some embodiments, the score determination module 1425 assigns the score to the user 115 as described at least with reference to FIG. 1.

The server 105 includes a content sharing module 1430 that can receive content from a user, e.g., user 115, of the culinary application 145 to be shared with other users of the culinary application 145 or with users in a social networking application. The content can include an image or a video of a meal prepared by a user using a recipe, e.g., recipe 125, provided by the culinary application 145. The content can include recipes, e.g., for dishes that are not in the culinary application 145. In some embodiments, the trivia generation module 1420 generates the trivia as described at least with reference to FIG. 1. Additional details with respect to the above modules are described at least with reference to FIG. 15 below.

Figure 15:
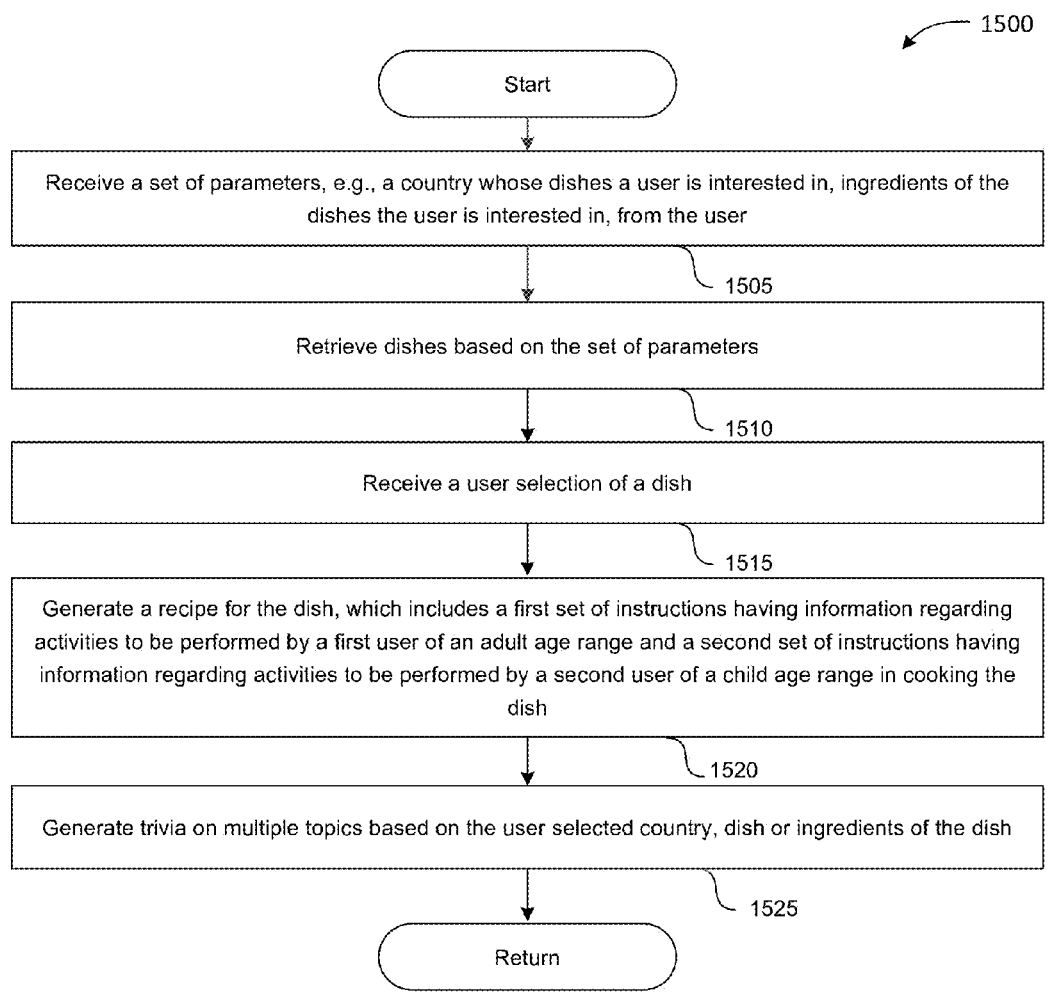
FIG. 15 is a flow diagram of a process for discovering recipes using a culinary application of FIG. 1, consistent with various embodiments.

FIG. 15 is a flow diagram of a process 1500 for discovering recipes using a culinary application of FIG. 1, consistent with various embodiments. In some embodiments, the process 1500 can be implemented in the environment 100 of FIG. 1. At block 1505, a parameters module 1405 of server 105, receives a set of parameters from a client, client 110, associated with a user, e.g., user 115, of the culinary application 145 for discovering recipes. In some embodiments, the parameters can be the set of parameters 120 and can include one or more of a country whose dishes the user 115 is interested in, the ingredients preferred by the user, etc. In some embodiments, the parameters module 1405 can receive the parameters as described at least with reference to FIG. 1 and FIGS. 3 and 5.

At block 1510, the search module 1410 can retrieve the dishes based on the parameters, e.g., the set of parameters 120, specified by the user 115 in block 1505. In some embodiments, the server 105 searches the storage system 155 based on the set of parameters and obtains a set of dishes.

At block 1515, the search module 1410 receives a user selection of the dish from the client 110.

At block 1520, the recipe generation module 1415 generates a recipe, e.g., recipe 125, of the user selected dish in a GUI at the client 110. The recipe generation module 1415 generates a first set of instructions that includes information regarding activities to be performed by the big chef 115a and a second set of instructions that includes information regarding activities to be performed by the little chef 115b. In some embodiments, the recipe generation module 1415 generates the first set of instructions as described at least in association with FIG. 9 and the second set of instructions as described at least in association with FIG. 10. In some embodiments, the recipe generation module 1415 generates the recipe 125 by using a corresponding recipe template, such as the example template 200 of FIG. 2, stored in the storage system 155.

At block 1525, the trivia generation module 1420 can generate trivia, e.g., trivia 130, associated with the recipe in the GUI at client 110. For example, the trivia can include information regarding one or more of a country of the dish, social issues in the country, ingredients of the dish, etc. The trivia can be on various topics, including math, science, social, geography, etc. The trivia generation module 1420 can present the trivia in various formats, e.g., in formats that are attractive to children of various age groups. The trivia generation module 1420 can present the trivia at various stages of recipe discovery process 1500, e.g., as described with reference to FIG. 1. In some embodiments, the trivia generation module 1420 can generate the trivia as described at least with reference to FIG. 1 and FIGS. 4A, 4B, 6-8 and 11.

Figure 16:
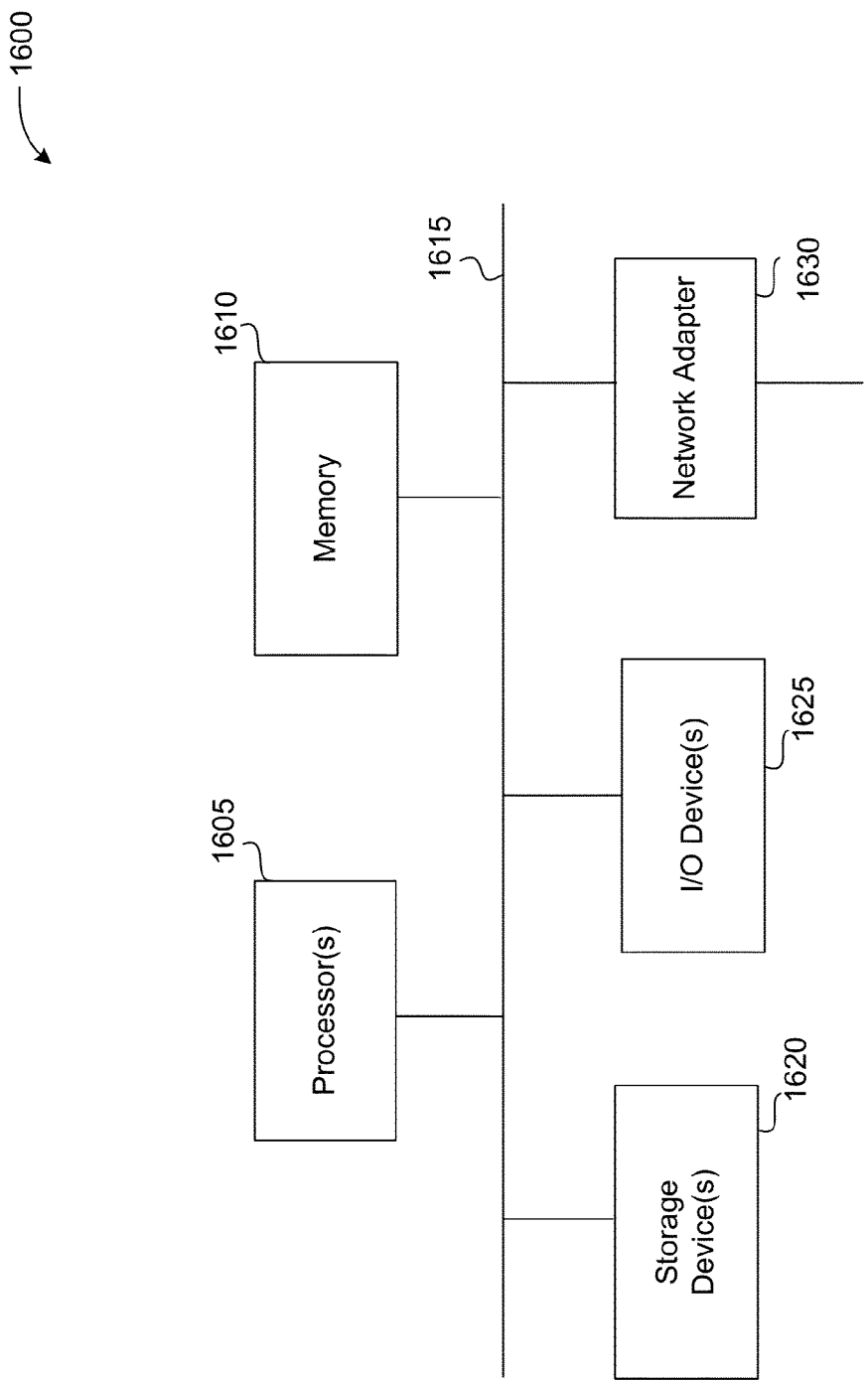
FIG. 16 is a block diagram of a computer system as may be used to implement features of some embodiments of the disclosed technology.

FIG. 16 is a block diagram of a computer system as may be used to implement features of some embodiments of the disclosed technology. The computing system 1600 may be used to implement any of the entities, components or services depicted in the examples of the foregoing figures (and any other components described in this specification). The computing system 1600 may include one or more central processing units ("processors") 1605, memory 1610, input/output devices 1625 (e.g., keyboard and pointing devices, display devices), storage devices 1620 (e.g., disk drives), and network adapters 1630 (e.g., network interfaces) that are connected to an interconnect 1615. The interconnect 1615 is illustrated as an abstraction that represents any one or more separate physical buses, point to point connections, or both connected by appropriate bridges, adapters, or controllers. The interconnect 1615, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The memory 1610 and storage devices 1620 are computer-readable storage media that may store instructions that implement at least portions of the described technology. In addition, the data structures and message structures may be stored or transmitted via a data transmission medium, such as a signal on a communications link. Various communications links may be used, such as the Internet, a local area network, a wide area network, or a point-to-point dial-up connection. Thus, computer-readable media can include computer-readable storage media (e.g., "non-transitory" media) and computer-readable transmission media.

The instructions stored in memory 1610 can be implemented as software and/or firmware to program the processor(s) 1605 to carry out actions described above. In some embodiments, such software or firmware may be initially provided to the computing system 1600 by downloading it from a remote system through the computing system 1600 (e.g., via network adapter 1630).

The technology introduced herein can be implemented by, for example, programmable circuitry (e.g., one or more microprocessors) programmed with software and/or firmware, or entirely in special-purpose hardwired (non-programmable) circuitry, or in a combination of such forms. Special-purpose hardwired circuitry may be in the form of, for example, one or more ASICs, PLDs, FPGAs, etc.

Remarks

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Terms that are used to describe the disclosure are discussed below, or elsewhere in the specification, to provide additional guidance to the practitioner regarding the description of the disclosure. For convenience, some terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms may on occasion be used interchangeably.

Consequently, alternative language and synonyms may be used for any one or more of the terms discussed herein, nor is any special significance to be placed upon whether or not a term is elaborated or discussed herein. Synonyms for some terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Those skilled in the art will appreciate that the logic illustrated in each of the flow diagrams discussed above, may be altered in various ways. For example, the order of the logic may be rearranged, substeps may be performed in parallel, illustrated logic may be omitted; other logic may be included, etc.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

I claim:

1. A method performed by a computing system, comprising:

outputting on a display associated with the computing system information regarding a plurality of countries in an application;

receiving a user selection of a country of the plurality of countries;

retrieving information regarding a plurality of dishes associated with the country;

receiving a user selection of a dish of the dishes;

retrieving, by the computing system, a recipe template based on the user selection, wherein the recipe template includes a list of ingredients, directions to prepare the dish, and trivia on a plurality of topics, the trivia related to at least one of the country, the dish, an ingredient of the dish, or the recipe; and adapting, by the computing system, the recipe template and the trivia to the second user, wherein the adapting includes:

identifying, in the recipe template, a first set of activities to be performed by a first user of an adult age range for preparing the dish, identifying, in the recipe template, a second set of activities to be performed by a second user of a child age range for preparing the dish, wherein the second set of activities is different from the first set of activities and are to be performed by the second user under the supervision of the first user, and determining, by the computing system, a content of the trivia that is suitable to the first user and that is suitable to the second user, wherein the determining includes generating a first description of the trivia that is suitable to the age range of the second user and a second description of the trivia that is suitable to the adult age range of the first user, configuring, by the computing system, a look and feel of a graphical user interface (GUI) to suit an age range of the second user, and generating, by the computing system, a recipe for the dish and the trivia in the GUI, the recipe including the first set of activities and the second set of activities, the trivia including the first description and the second description.

2. The method of claim 1, wherein the topics include at least one of math, science, geography or social responsibility.

3. The method of claim 1, wherein generating the recipe and the trivia includes:
generating at least a portion of the trivia before the recipe is generated, the portion of the trivia including a link to recipe,
receiving a user selection of the link, and
generating the recipe in response to the user selection of the link.

4. The method of claim 1, wherein generating the recipe and the trivia includes generating at least a portion of the trivia as a quiz on at least one of the plurality of topics, the quiz eliciting a first response from the second user.

5. The method of claim 4 further comprising:
receiving the response from the second user, and
assigning a score to the second user in response to receiving the first response.

6. The method of claim 1 further comprising:
generating the GUI based on a theme.

7. The method of claim 6 wherein generating the GUI based on the theme includes generating a plurality of multimedia components of the GUI based on at least one of the country, the dish, an ingredient of the dish, or the recipe.

8. The method of claim 1, wherein receiving the user selection of the dish includes:
receiving a user selection of a plurality of ingredients,
determining a set of the dishes that include one or more of the ingredients, and
receiving one of the set of the dishes as the dish.

9. The method of claim 1 further comprising:
receiving, from the first or the second user, an image of the dish prepared based on the recipe; and
posting the image to a social networking application of the first user.

10. The method of claim 9 further comprising:
assigning a score to the first user or the second user in response to posting the image to the social networking application.

11. A method performed by a computing system, comprising:
receiving a user selection of a country of a plurality of countries;
retrieving information regarding a plurality of dishes associated with the country;
receiving a user selection of a set of ingredients;
identifying a set of the dishes from the plurality of dishes that includes the set of ingredients;
receiving a user selection of a dish of the set of the dishes;
retrieving trivia on at least one of a plurality of topics based on at least one of the country, the dish or the set of ingredients;
retrieving a recipe for the dish, the recipe including a first set of activities to be performed by a first user of an adult age range for preparing the dish and a second set of activities to be performed by a second user of a child age range for preparing the dish, wherein the second set of activities is different from the first set of activities; and
generating, by the computing system, the trivia and the recipe in a GUI on a computing device by adapting the recipe to the second user, the adapting including:
changing, by the computing system, a look and feel of the GUI to suit an age range of the second user, and
formatting, by the computing system, the trivia to generate (a) a first description of the trivia that is suitable to the adult age range of the first user and (b) a second description of the trivia that is suitable to the age range of the second user, and
outputting the recipe in the GUI after receiving an indication from the computing device that the trivia presented on at least one of the topics in the GUI is viewed by the second user.

12. The method of claim 11, wherein generating the trivia and the recipe includes:
generating information that includes instructions for the first user to guide the second user in performing the activities for preparing the dish.

13. The method of claim 11, wherein outputting the recipe in the GUI after receiving the indication includes:
generating the trivia with a link,
receiving a user selection of the link associated with the trivia, and
outputting the recipe on the GUI in response to receiving the user selection of the link.

14. A non-transitory computer-readable storage medium storing computer-readable instructions, the instructions comprising:
instructions for receiving, by a server computing device, a user selection of a country from a plurality of countries;
instructions for receiving, by the server computing device, a user selection of a dish from a plurality of dishes associated with the country;
instructions for retrieving, by the server computing device, trivia on at least one of a plurality of topics based on at least one of the country, the dish or ingredients of the dish;
instructions for retrieving, by the server computing device, a recipe for the dish, the recipe including a first set of activities to be performed by a first user of an adult age range for preparing the dish and a second set of activities to be performed by a second user of a child age range for preparing the dish, wherein the second set of activities is different from the first set of activities and are activities that are to be performed by the second user under the supervision of the first user; and
instructions for outputting, by the server computing device, the recipe with trivia on a plurality of topics in a GUI on a client computing device by adapting the recipe to the second user, the recipe output in the GUI after the second user has viewed at least a portion of the trivia, the adapting including:

changing, by the server computing device, a look and feel of the GUI to suit an age range of the second user, and formatting, by the server computing device, the trivia to generate (a) a first description of the trivia that is suitable to the adult age range of the first user and (b) a second description of the trivia that is suitable to the age range of the second user.

15. The non-transitory computer-readable storage medium of claim 14, wherein the topics include any of math, science, geography or social responsibility.

16. The non-transitory computer-readable storage medium of claim 14, wherein the instructions for receiving the user selection of the dish include instructions for:

receiving information regarding an ingredient that is available with the user, filtering the dishes to identify a set of the dishes that includes the ingredient, and receiving one of the set of the dishes as the dish.

17. The non-transitory computer-readable storage medium of claim 14, wherein the instructions for receiving the user selection of the dish include instructions for:

receiving an indication that at least one of the ingredients is unavailable, and generating, in response to receiving the indication, an order request for purchasing the at least one of the ingredients, the order request generated via a third party application and transmitted to a server associated with the third party application.

18. The non-transitory computer-readable storage medium of claim 14, wherein the instructions for outputting the recipe and the trivia in the GUI include instructions for:

generating the trivia with a link, receiving a user selection of the link associated with the trivia, and outputting the recipe on the GUI in response to receiving the user selection of the link.

19. The non-transitory computer-readable storage medium of claim 14, wherein the instructions for outputting the recipe and the trivia in the GUI include instructions for:

generating the trivia as a quiz on at least one of the plurality of topics, the quiz eliciting a first response from the second user.

20. The non-transitory computer-readable storage medium of claim 19 further comprising instructions for:

receiving the first response from the second user, and assigning a score to the second user in response to receiving the first response.

21. The non-transitory computer-readable storage medium of claim 14, wherein the instructions for outputting the recipe with trivia in the GUI include instructions for generating GUI based on a theme, the theme determined based on at least one of the country, the dish, an ingredient of the dish, or the recipe.

22. The non-transitory computer-readable storage medium of claim 14, wherein the instructions for retrieving trivia on at least one of the topics include instructions for generating nutritional information of an ingredient of the dish.

23. The non-transitory computer-readable storage medium of claim 14, wherein the instructions for retrieving trivia on at least one of the topics include instructions for generating information on the country the dish is associated with.

24. A system, comprising:
a processor;

a parameters module configured to:

generate information regarding a plurality of countries in a GUI on a computing device and receive a user selection of a country of the plurality of countries, generate information regarding a plurality of ingredients in the GUI and receive a user selection of one or more of the ingredients, and generate information regarding a plurality of dishes associated with the country in the GUI and receive a user selection of a dish of the dishes, wherein the plurality of dishes are dishes that include one or more of the ingredients;

a search module configured to retrieve a recipe for the dish, the recipe including a first set of activities to be performed by a first user of an adult age range for preparing the dish and a second set of activities to be performed by a second user of a child age range for preparing the dish, wherein the second set of activities is different from the first set of activities and are activities that are to be performed by the second user under the supervision of the first user; and a recipe generation module configured to generate the recipe in the GUI by adapting the recipe to the second user, wherein the recipe generation module is configured to adapt the recipe by:

changing a look and feel of the GUI to suit an age range of the second user; and a trivia generation module configured to generate trivia associated with the recipe in the GUI by adapting the trivia to the second user, wherein the trivia generation module is configured to adapt the trivia by:

formatting the trivia to generate (a) a first description of the trivia that is suitable to the adult age range of the first user and (b) a second description of the trivia that is suitable to the age range of the second user.

25. The system of claim 24, wherein the search module is configured to retrieve the trivia on at least one of a plurality of topics the trivia based on at least one of the country, the dish or the one or more of the ingredients.

26. The system of claim 25, wherein the recipe generation module is configured to generate the recipe in the GUI after receiving an indication from the client computing device that the trivia on at least one of the topics presented in the GUI is viewed by the second user.

27. The system of claim 24 further comprising:
a content sharing module configured to receive, from the first or the second user, an image of the dish prepared based on the recipe and post the image to a social networking application of the first user.

28. The system of claim 24 further comprising:
a score determination module to determine a score for the second user based on a plurality of activities performed by the second user, the activities including any of (a) answering a quiz of trivia presented in the GUI, the quiz based on at least one of the country, the dish, the recipe or the one or more of the ingredients, (b) posting an image of the dish prepared based on the recipe to a social networking application, or (c) uploading a first recipe for a first dish.

29. The system of claim 24 further comprising:
a content sharing module to receive a first recipe of a first dish from the computing device, the content sharing module further configured to share the first recipe with a plurality of users in a social networking application.

* * * * *